United States Patent
Peterson et al.

(10) Patent No.: US 11,407,699 B2
(45) Date of Patent: Aug. 9, 2022

(54) METHODS OF MAKING MODIFIED ALCOHOL CONTAINING PRODUCTS

(71) Applicant: SPIRITED BEVTECH LLC, Upper Arlington, OH (US)

(72) Inventors: Devin Grant Peterson, Upper Arlington, OH (US); Smaro Kokkinidou, Minneapolis, MN (US)

(73) Assignee: SPIRITED BEVTECH LLC, Upper Arlington, OH (US)

( * ) Notice: Subject to any disclaimer, the term of this patent is extended or adjusted under 35 U.S.C. 154(b) by 0 days.

(21) Appl. No.: 16/522,091

(22) Filed: Jul. 25, 2019

(65) Prior Publication Data

US 2020/0148613 A1 May 14, 2020

Related U.S. Application Data

(63) Continuation of application No. 15/305,299, filed as application No. PCT/US2015/026929 on Apr. 21, 2015, now abandoned.

(60) Provisional application No. 61/982,228, filed on Apr. 21, 2014.

(51) Int. Cl.
| | |
|---|---|
| C07C 29/132 | (2006.01) |
| C12H 1/044 | (2006.01) |
| C12H 1/07 | (2006.01) |
| A61Q 11/00 | (2006.01) |
| A61K 8/34 | (2006.01) |
| A61K 31/045 | (2006.01) |
| C12H 1/056 | (2006.01) |

(52) U.S. Cl.
CPC .............. *C07C 29/132* (2013.01); *A61K 8/34* (2013.01); *A61K 31/045* (2013.01); *A61Q 11/00* (2013.01); *C12H 1/0408* (2013.01); *C12H 1/0424* (2013.01); *C12H 1/063* (2013.01)

(58) Field of Classification Search
CPC .... C12H 1/0408; C12H 1/0424; C12H 1/063; A61Q 11/00; A61K 8/34; A61K 31/045; C07C 29/132
USPC ....................................................... 426/592
See application file for complete search history.

(56) References Cited

U.S. PATENT DOCUMENTS

| | | | |
|---|---|---|---|
| 3,914,442 A | 10/1975 | Servadio et al. | |
| 2006/0292262 A1 | 12/2006 | Asakawa | |
| 2010/0009057 A1* | 1/2010 | Simonetto | C12G 3/06 426/592 |
| 2012/0028333 A1 | 2/2012 | Piatesi et al. | |
| 2013/0058887 A1 | 3/2013 | Nakayama et al. | |
| 2017/0036974 A1 | 2/2017 | Peterson et al. | |

FOREIGN PATENT DOCUMENTS

| | | | |
|---|---|---|---|
| BG | 48744 A1 | 5/1991 | |
| BG | 50503 A3 | 8/1992 | |
| BG | 95890 A | 1/1994 | |
| BG | 98296 A | 8/1994 | |
| CA | 2052435 C | 12/2002 | |
| CN | 101434900 B | 5/2013 | |
| JP | 2006187213 A | 7/2006 | |
| JP | 2012100651 A | 5/2012 | |
| NZ | 539616 A | 5/2007 | |
| RU | 2003672 C1 | 11/1993 | |
| RU | 2034916 C1 | * | 5/1995 |
| RU | 2034916 C1 | 5/1995 | |
| RU | 2130064 C1 | 5/1999 | |
| RU | 2130065 C1 | 5/1999 | |
| RU | 2238313 C1 | 10/2004 | |
| RU | 2272831 C1 | 3/2006 | |
| RU | 2382074 C2 | 2/2010 | |
| WO | 2004031341 A1 | 4/2004 | |
| WO | 2005102071 A1 | 11/2005 | |

OTHER PUBLICATIONS

"Sensory Properties of Beverage Products (Alcoholic and Nonalcoholic)", Chapter 13, A Handbook for Sensory and Consumer-Driven New Product Development, http://dx.doi.org/10.1016/B978-0-08-100352-7.00013-0, 281-304 (2017).
"Using Sodium Carbonate/Bicarbonate in stripped product (self. firewater)", http://www.reddit.com/r/firewater/comments/2pj3wr/using_sodium_carbonatebicarbonate_in_stripped, 6 pages (downloaded Jan. 27, 2016).
Biernacka, P , et al., "Volatile composition of raw spirits of different botanical origin", J Inst Brew 118, 393-400 (2012).
Curylo, J , et al., "Application of Single Drop Extraction (SDE) Gas Chromatography Method for the Determination of Carbonyl Compounds in Spirits and Vodkas", Analytical Letters 39(13), 2629-2642 (2006).
Hayman, C , "Vodka", Encyclopedia of Food Sciences and Nutrition (Second Edition), pp. 6068-6069 (2003).
Home Distillation , www.homedistiller.org/distill/dtw/strip, 4 pages (downloaded Feb. 12, 2016).
Home Distiller , http://homedistiller.org/forum/viewtopic.php?f=15&t=22130, 5 pages (downloaded Jan. 27, 2016).

(Continued)

*Primary Examiner* — Vera Stulii

(74) *Attorney, Agent, or Firm* — Viksnins Harris Padys Malen LLP

(57) ABSTRACT

Certain embodiments of the invention provide a method of preparing a modified distilled alcoholic spirit, comprising contacting a corresponding starting distilled alcoholic spirit with a base under conditions that cause at least one free carbonyl compound in the starting distilled alcoholic spirit to be reduced, to provide the modified distilled alcoholic spirit that has at an alcohol by volume (ABV) of at least 15%. Certain embodiments also provide a modified distilled alcoholic spirit prepared by the methods described herein.

26 Claims, 12 Drawing Sheets

(56) References Cited

OTHER PUBLICATIONS

Lachenmeier, D , et al., "The use of ion chromatography to detect adulteration of vodka and rum", Eur Food Res Technol 218(1), 105-110 (2003).

Making Vodka , https://www.stilldragon.org/discussion/1035/making-vodka, 50 pages (downloaded Jan. 27, 2016).

Monakhova, Y , et al., "Application of automated eightfold suppression of water and ethanol signals in 1H NMR to provide sensitivity for analyzing alcoholic beverages", Magn Reson Chem. 49(11), 734-739 (2011).

Ng, L., et al., "Characterisation of Commercial Vodkas by Solid-Phase Microextraction and Gas Chromatography/Mass Spectrometry Analysis", J. Sci. Food Agric., 70(3), 380-388 (1996).

Patent Cooperation Treaty , International Searching Authority, Search Report and Written Opinion for PCT/US2015/26929, 13 pages, dated Aug. 28, 2015.

Perry, D , "Odour intensities of whisky compounds", In Distilled Beverage flavor: Recent developments. Piggot, JR and Paterson, A. Ellis Horwood, Chichester, UK, pp. 200-207 (1989).

Perry, D , "Whisky Maturation Mechanisms", In Proc. 2nd Aviemore Conf. Malt Brew Distilling, (eds) Campell and Priest, Institute of Brewing, London, pp. 409-412 (1986).

Qian, M., et al., "Gas Chromatography", Food Analysis, p. 513-537 (2010).

Rosentrater and Evers , "Malting, brewing, fermentation, and distilling", Chapter 12, in Kent's Technology of Cereals (Fifth Edition), pp. 729-784 (2018).

Russell, I , et al., "Whisky", Technology, Production and Marketing, Elsevier Ltd, 341 pages (2003).

Zhao, D , et al., "Intracellular antioxidant effect of vanillin, 4-methylguaiacol and 4-ethylguaiacol: three components in Chinese Baijiu", RSC Adv 7, 46395, 11 pages (2017).

\* cited by examiner

US 11,407,699 B2

METHODS OF MAKING MODIFIED ALCOHOL CONTAINING PRODUCTS

RELATED APPLICATION

This application is a continuation of U.S. application Ser. No. 15/305,299, which is a 35 U.S.C. § 371 application of International Application Serial No. PCT/US2015/026929, filed Apr. 21, 2015, which claims the benefit of U.S. Provisional Application Ser. No. 61/982,228, filed Apr. 21, 2014. The entire content of these applications are hereby incorporated by reference herein.

BACKGROUND OF THE INVENTION

Flavor is a complex sensation. The chemical stimuli of a flavor response typically consist of numerous compounds. Flavor compounds are commonly categorized into different modalities such as taste (gustation; sweet, sour, salty, bitter, umami), aroma (olfaction) and chemesthetic (chemical irritation of trigeminal nerves—heat, cooling, pain) sensations. Ethyl alcohol and alcoholic products as manufactured have a characteristic burn flavor (chemestetic sensation) that is distinct from aroma or taste, and which is typically viewed as a negative product attribute. Currently there is a need for methods able to modify alcohol containing products resulting in reduction of this burn flavor. In particular, there is a need for methods to modify distilled alcoholic spirits that are not typically processed by purification techniques beyond distillation (e.g., filtration), such as whiskey, rum, brandy, tequila, gin and other alcoholic distilled spirits to reduce this trigeminal burn sensation typically associated with alcohol. Additionally there is a need to develop processing technologies that can accelerate the aging process of distilled alcoholic spirits that contribute to favorable flavor changes, such as improving smoothness perception and reducing burn flavor. In particular, there is a need for methods for "accelerated aging" for products such as brandy and whiskey which require years of aging thus, reducing production cost whilst maintaining the sensory quality of the final product.

SUMMARY OF THE INVENTION

Accordingly, the invention provides methods for modifying alcoholic products to reduce burn flavor. In particular, these methods modify distilled alcoholic spirits, such as whiskey, rum, brandy, tequila, soju, gin, baijiu and other alcoholic distilled spirits, which are typically not processed by purification techniques, to reduce burn flavor. In addition to reducing alcohol burn, these methods may also positively impart maturation and result in a more desirable smoothness perception, cleaner overall flavor profile and/or increased consumer palatability. In certain embodiments, these results may be obtained without the addition of high amounts of sweeteners (sugars, high intensity sweeteners, etc.).

Certain embodiments of the invention provide a method of preparing a modified distilled alcoholic spirit, comprising contacting a corresponding starting distilled alcoholic spirit with a base under conditions that cause at least one free carbonyl compound in the starting distilled alcoholic spirit to be reduced, to provide the modified distilled alcoholic spirit that has an alcohol by volume (ABV) of at least about 15%.

Certain embodiments of the invention provide a method of preparing a modified distilled alcoholic spirit, comprising contacting a corresponding starting distilled alcoholic spirit with a base under conditions that cause the total of free carbonyl compounds in the starting distilled alcoholic spirit to be reduced, to provide the modified distilled alcoholic spirit that has an alcohol by volume (ABV) of at least about 15%.

Certain embodiments of the invention provide a modified distilled alcoholic spirit prepared by the methods described herein.

Certain embodiments of the invention provide a modified distilled alcoholic spirit comprising at least one free carbonyl compound, wherein the at least one free carbonyl compound is reduced as compared to a corresponding unmodified distilled alcoholic spirit.

Certain embodiments of the invention provide a non-aged distilled alcoholic spirit with a pH greater than or equal to about 7.

Certain embodiments of the invention provide a method of preparing a modified mouthwash comprising providing a corresponding starting mouthwash with a pH less than about 5.5 and contacting it with a base to provide a modified mouthwash with a pH greater than about 6.

Certain embodiments of the invention provide a modified mouthwash prepared by the methods described herein.

Certain embodiments of the invention provide a modified mouthwash comprising at least one free carbonyl compound, wherein the at least one free carbonyl compound is reduced as compared to a corresponding unmodified mouthwash.

Certain embodiments of the invention provide a mouthwash with a pH greater than about 6 and an alcohol by volume content of at least 5%.

Certain embodiments of the invention provide a method of preparing a modified medicament comprising providing a corresponding starting medicament with a pH less than about 5 and contacting it with a base to provide a modified medicament with a pH greater than about 6, wherein the modified medicament has an alcohol by volume of at least about 5%.

Certain embodiments of the invention provide a modified medicament prepared by the methods described herein.

Certain embodiments of the invention provide a modified medicament comprising at least one free carbonyl compound, wherein the modified medicament has an alcohol by volume of at least about 5%; and wherein the at least one free carbonyl compound is reduced as compared to a corresponding unmodified medicament.

Certain embodiments of the invention provide a medicament with a pH greater than about 5 and an alcohol by volume content of at least about 5%.

Certain embodiments of the invention provide a method of preparing a modified beer, comprising contacting a corresponding starting beer with a base under conditions that cause at least one free carbonyl compound in the starting beer to be reduced, to provide the modified beer.

Certain embodiments of the invention provide a modified beer prepared by the methods described herein.

DETAILED DESCRIPTION

Figure 1:
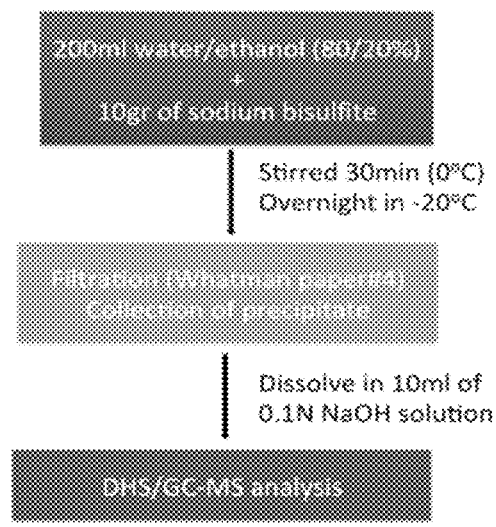
FIG. 1. Experimental protocol for carbonyl species scavenging and sensory evaluation of water/ethanol samples. Acetaldehyde was added as internal standard prior to trapping at levels of 5 mM.

Certain embodiments of the invention provide methods to reduce the burn flavor attributes of ethyl alcohol and alcohol-containing products, such as oral care and hygiene products (e.g., mouthwash), medicaments (e.g., cough medicine, expectorant syrups), and spirits (e.g., whiskey, rum and brandy). Ethyl alcohol and alcoholic products as manufactured have a characteristic burn flavor (chemestetic sensation) that is typically viewed as a negative product attribute. As described herein, the burn of ethyl alcohol is not mainly due to ethyl alcohol itself as previously thought but is largely influenced by the chemical composition (i.e. carbonyl compounds) of the product. By altering the chemical composition of ethyl alcohol, specifically the free carbonyl compounds (i.e. aldehydes and ketones), the perceived burn intensity of ethyl alcohol and alcoholic containing products can be modified. The chemical composition of carbonyl compounds in ethyl alcohol can be altered by 1) adjusting the pH of the product; 2) the addition of compounds or scavenger agents that react with aldehydes/ketones and thereby decrease the free concentration of aldehydes/ketones (i.e. acetal reactions); 3) extraction/isolation/filtration techniques that remove aldehydes/ketones; 4) or a combination of these techniques.

As described herein, an equilibrium reaction exists between carbonyl compounds and alcohols (reactants) to hemiacetals and acetals (products) that is pH dependent in ethyl alcohol and alcoholic products, such as distilled spirits. Both saturated and unsaturated aldehydes (and ketones) are reactive and will react with alcohol containing compounds (i.e. ethyl alcohol) to form hemi-acetals/acetals (or hemi-ketals/ketals) and the equilibrium of this reaction is pH dependent. At a lower pH values, the equilibrium favors the free "carbonyls" (aldehydes and ketones) and consequently lower levels of hemi-acetals/acetals (or hemi-ketals/ketals) products. At higher pH values, the equilibrium favors hemi-acetals/acetals formation and consequently lower levels of free "carbonyls" (aldehydes and ketones). If the pH of the alcoholic product is increased (range from 2-12), the concentration of free carbonyls will decrease, and the ethyl alcohol or alcohol-containing product will have lower burn intensity (smoother flavor). This equilibrium can additionally be beneficial as the increased acetal species can positively impart smoothness and maturation, as they are associated with pleasant aroma attributes contrary to their pungent aldehyde counterparts. This improved alcohol flavor (less burn) has been demonstrated by increasing the pH with economical food grade ingredients, such as sodium hydroxide, sodium carbonate and sodium bicarbonate (see, Examples). This has been shown using analytical experiments that show lower levels of aldehydes exist at a higher product pH and through sensory analysis (human analysis), which confirmed these samples (e.g., vodka, brandy, ethyl alcohol, mouthwash) had a perceived lower alcohol burn intensity. Additionally, as described herein, the addition of select alcoholic compounds, such as trehalose, also causes a reduction in alcohol burn (e.g., by reducing carbonyls).

In certain embodiments of the invention, the methods target a reduction of alcohol burn and result in a more desirable smoothness perception, cleaner overall flavor profile and/or increased consumer palatability. In certain embodiments, these results may be obtained without the addition of high amounts of sweeteners (e.g., sugars, high intensity sweeteners, etc.).

Distilled Alcoholic Spirits

Certain embodiments of the invention provide a method of preparing a modified distilled alcoholic spirit, comprising contacting a corresponding starting distilled alcoholic spirit with a base under conditions that cause at least one free carbonyl compound in the starting distilled alcoholic spirit to be reduced, to provide the modified distilled alcoholic spirit that has an alcohol by volume (ABV) of at least about 15%. In certain embodiments, the distilled alcoholic spirit has an ABV of at least about 20%, at least about 30%, at least about 40%, at least about 45% or more.

Certain embodiments of the invention provide a method of preparing a modified distilled alcoholic spirit, comprising contacting a corresponding starting distilled alcoholic spirit with a base under conditions that cause the total of free carbonyl compounds in the starting distilled alcoholic spirit to be reduced, to provide the modified distilled alcoholic spirit that has an alcohol by volume (ABV) of at least about 15%. In certain embodiments, the distilled alcoholic spirit has an ABV of at least about 20%, 30%, 40%, 45% or more.

In certain embodiments, a distilled alcoholic spirit is any beverage comprising alcohol, which is produced by distillation of a mixture produced from alcoholic fermentation, such as wine. For example, in certain embodiments, the distilled alcoholic spirit may be whiskey, rum, brandy, tequila, soju, gin or baiju. In certain embodiments, the distilled alcoholic spirit is not vodka.

Typically, a whiskey is an alcoholic distillate from a fermented mash of grain produced at less than 190° proof (i.e., 95% ABV) in such manner that the distillate possesses the taste, aroma, and characteristics generally attributed to whisky, stored in oak containers (except that corn whisky need not be so stored), and bottled at not less than 80° proof (i.e., 40% ABV), and also includes mixtures of such distillates for which no specific standards of identity are prescribed (see, e.g., 27 C.F.R. § 5.22, which provides standards of identity for certain classes and types of distilled spirits). In certain embodiments, the whiskey may be a bourbon whiskey, a rye whiskey, a wheat whiskey, a malt whiskey, a rye malt whiskey, a corn whiskey, straight bourbon whiskey, a straight rye whiskey, a straight wheat whiskey, a straight malt whiskey, a straight rye malt whiskey, a straight corn whiskey, a whisky distilled from bourbon (rye, wheat, malt, or rye malt) mash, a light whisky, a blended whisky, a blend of straight whiskies, a spirit whisky, a scotch whisky, an Irish whisky, or a Canadian whisky.

Typically, a rum is an alcoholic distillate from the fermented juice of sugar cane, sugar cane syrup, sugar cane molasses, or other sugar cane by-products, produced at less than 190° proof (i.e., 95% ABV) in such manner that the distillate possesses the taste, aroma, and characteristics generally attributed to rum, and bottled at not less than 80° proof (i.e., 40% ABV); and also includes mixtures solely of such distillates (see, e.g., 27 C.F.R. § 5.22).

Typically, a brandy is an alcoholic distillate from the fermented juice, mash, or wine of fruit, or from the residue thereof, produced at less than 190° proof (i.e., 95% ABV) in such manner that the distillate possesses the taste, aroma, and characteristics generally attributed to the product, and bottled at not less than 80° proof (i.e., 40% ABV) (see, 27 C.F.R. § 5.22). In certain embodiments, the brandy may be a fruit brandy, cognac or cognac (grape) brandy, dried fruit brandy, lees brandy, pomace brandy or marc brandy, residue brandy, neutral brandy, eau de vie (i.e., a clear fruit brandy, such as, e.g., snap) or a substandard brandy.

Typically, tequila is an alcoholic distillate from a fermented mash derived, e.g., principally from the Agave Tequilana Weber ("blue" variety), with or without additional fermentable substances, distilled in such a manner that the distillate possesses the taste, aroma, and characteristics generally attributed to Tequila and bottled at not less than 80° proof (i.e., 40% ABV), and also includes mixtures solely of such distillates. Generally, tequila is a distinctive product of Mexico, manufactured in Mexico in compliance with the laws of Mexico regulating the manufacture of Tequila for consumption in that country (see, e.g., 27 C.F.R. § 5.22).

Typically, soju refers to a distilled beverage that is native to Korea. It is traditionally made from rice, wheat, barley, as well as other starches, such as potatoes, sweet potatoes, or tapioca depending on the desired sweetness of the end product. Soju is typically a clear and colorless distilled beverage and its alcohol content may vary from about 16.7%, to about 45% alcohol by volume (ABV) with 20% ABV being most popular. Soju may be produced by two different ways to yield distilled and diluted soju. The classic way of distilling soju uses a single distillation method yielding a higher alcohol content spirit and the modern way of diluted soju that uses the chain distillation method to yield a spirit with lower ABV (~20%). Addition of sugar during the distillation step(s) is also common practice affording the beverage sweet taste. The addition of sugar, the variable distillation methods employed and final alcohol content differentiates soju from vodka, which generally has a minimum ABV of 37.5%.

Typically, gin is a product obtained by original distillation from mash, or by redistillation of distilled spirits, or by mixing neutral spirits, with or over juniper berries and other aromatics, or with or over extracts derived from infusions, percolations, or maceration of such materials, and includes mixtures of gin and neutral spirits. It typically derives its main characteristic flavor from juniper berries and is bottled at not less than 80° proof (i.e., 40% ABV). Gin produced exclusively by original distillation or by redistillation may be further designated as "distilled". In certain embodiments, the gin may be "Dry gin" (London dry gin), "Geneva gin" (Hollands gin), or "Old Tom gin" (Tom gin).

Typically, baiju refers to a distilled spirit produced predominantly in China. Generally it is produced through fermentation and distillation of sorghum or rice, but sometimes other grains, legumes, vegetables or fruit is used to produce a spirit with an alcohol by volume (ABV) content of 40-60%. The jiuqu starter culture used in the production of baijiu mash, or more commonly known as Qu, is usually made of pulverized wheat grains and can contain Chinese medicinal herbs, mixed with water and formed into bricks or balls that are stored in a warm, damp environment for about a month. The Qu is then filled with yeasts, fungi and other types of microorganisms to merge saccharification and fermentation steps for production of alcohol. Fermentation of Baijiu takes places in subterranean mud pits, ceramic jars or in jars buried underground and can be single or multiple cycle process. When fermentation is complete distillation takes place to yield baijiu. After distillation, baijiu is commonly aged in earthenware urns in underground cellars, caves or dark rooms for at least one to two years. Once the baijiu is aged, the desired amount is bottled or diluted to taste and to achieve an ABV of 40-60% (most commonly 48-56%).

In certain embodiments, the distilled alcoholic spirit is whiskey. In certain embodiments, the distilled alcoholic spirit is rum. In certain embodiments, the distilled alcoholic spirit is brandy (e.g., eau de vie). In certain embodiments, the distilled alcoholic spirit is tequila. In certain embodiments, the distilled alcoholic spirit is gin. In certain embodiments, the distilled alcoholic spirit is baiju. In certain embodiments, the distilled alcoholic spirit is soju.

In certain embodiments, the pH of the starting distilled alcoholic spirit is about 2.5 to about 5.5 (e.g., about 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4 or 5.5).

In certain embodiments, the pH of the starting distilled alcoholic spirit is about 2.5 to about 4.5 (e.g., about 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4 or 4.5).

In certain embodiments, the pH of the starting distilled alcoholic spirit is about 3 to about 5.5 (e.g., about 3.0, 3.1, 3.2, 3.3, 3.4, 3.5, 3.6, 3.7, 3.8, 3.9 4.0, 4.1, 4.2, 4.3, 4.4, 4.5, 4.6, 4.7, 4.8, 4.9, 5.0, 5.1, 5.2, 5.3, 5.4 or 5.5).

In certain embodiments, the pH of the starting distilled alcoholic spirit is about 3 to about 4.4 (e.g., about 3.0, 3.1, 3.2, 3.3, 3.4, 3.5, 3.6, 3.7, 3.8, 3.9 4.0, 4.1, 4.2 or 4.3).

In certain embodiments, the pH of the modified distilled alcoholic spirit is about 5 to about 12 (e.g., about 5, 5.5, 6, 6.5, 7, 7.5, 8, 8.5, 9, 9.5, 10, 10.5, 11, 11.5 or 12).

In certain embodiments, the pH of the modified distilled alcoholic spirit is about 5.5 to about 12 (e.g., about 5.5, 6, 6.5, 7, 7.5, 8, 8.5, 9, 9.5, 10, 10.5, 11, 11.5 or 12).

In certain embodiments, the pH of the modified distilled alcoholic spirit is about 6 to about 8.5 (e.g., about 6, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5).

As used herein, a base is a substance (e.g., in a solid or liquid form) that will increase the pH of the starting distilled alcoholic spirit. In certain embodiments, the base is a solid. In certain embodiments, the base is a liquid. In certain embodiments, the base is a food grade additive. In certain embodiments, the base is sodium bicarbonate, sodium carbonate, sodium hydroxide, potassium hydroxide, potassium carbonate or potassium bicarbonate. In certain embodiments, the base is sodium carbonate.

In certain embodiments, the at least one free carbonyl compound is reduced by at least about 10, 20, 25, 30, 35, 40, 45, 50, 55, 60, 65, 70, 75, 80, 85, 90, 95, 96, 97, 98, or 99% by weight. In certain embodiments, the at least one free carbonyl compound is reduced by at least about 10% by weight. In certain embodiments, the at least one free carbonyl compound is reduced by at least about 20% by weight.

In certain embodiments, more than one free carbonyl compound is reduced.

In certain embodiments, the total of the free carbonyl compounds is reduced by at least about 10% by weight. Accordingly, as used herein, the total weight of the free carbonyl compounds in the starting distilled alcoholic spirit must be reduced by about 10% (e.g., certain free carbonyl species may be reduced while other species may be unchanged or increased). In certain embodiments, the total of the free carbonyl compounds is reduced by at least about 20% by weight. Accordingly, as used herein, the total weight of the free carbonyl compounds in the starting distilled alcoholic spirit must be reduced by about 20% (e.g., certain free carbonyl species may be reduced while other species may be unchanged or increased). In certain embodiments, the total of the free carbonyl compounds is reduced by at least about 10, 15, 20, 25, 30, 35, 40, 45, 50, 55, 60, 65, 70, 75, 80, 85, 90, 95, 96, 97, 98, or 99% by weight.

Quantitative changes in levels of free carbonyl compounds (e.g., aldehydes or ketones) and other relevant chemical species (e.g., acetals, hemi-acetals, ketals or hemiketals) can be determined by one skilled in the art using common analytical methods for volatile analysis known in the art, such as Gas Chromatography-Mass Spectroscopy (GC-MS) coupled with various sample preparation methods, such as Headspace, solvent extraction or distillation methods. (D G. Peterson, G A Reineccius and M C Qian (2010). *Gas Chromatography*. In S. S. Nielsen (Ed.), *Food Analysis* (4$^{th}$ *Ed.*) (p.p. 513-537). New York, N.Y. Springer Science+Business Media LLC.). Additionally, techniques such as Nuclear Magnetic Resonance spectroscopy (NMR) can be used to qualitatively confirm changes of free carbonyl compounds. Examples of methods for measuring both qualitative and quantitative changes are presented below in Examples 1, 2 and 3.

As used herein a free carbonyl compound includes aldehydes and ketones comprising a C(=O) functional group.

In certain embodiments, at least one free carbonyl compound is an aldehyde. One skilled in the art would understand that an aldehyde includes compounds of formula: $R_xCHO$. In certain embodiments, at least one aldehyde is selected from acetaldehyde, 2-methylbutanal, 3-methylbutanal, propanal, butanal, pentanal, hexanal, heptanal, octanal, nonanal, decanal and benzaldehyde, as well as, unsaturated aldehydes such as 2-propenal, 3-methyl-2-butenal, (E)-2-hexanal, (E)-2-octenal, (E)-2-nonenal and (E,E)-2,4-decadienal.

In certain embodiments, the at least one free carbonyl compound is a ketone. One skilled in the art would understand that a ketone includes compounds of formula: $R_xC(=O)R_x$. In certain embodiments, the at least one ketone is selected from 2-butanone, 2-pentanone, 2-heptanone, 2,3-butendione and 2,3-pentendione.

In certain embodiments, the at least one free carbonyl compound in the starting distilled alcoholic spirit is reduced through a conversion to an acetal. One skilled in the art would understand that an acetal includes compounds of formula: $R_x—C(OR_x)_2H$. In certain embodiments, the at least one acetal is selected from acetaldehyde diethyl acetal, 2-methyl butanal diethyl acetal, 2-methylpropanal diethyl acetal, 1,1,3,-triethoxypropane, acetaldehyde di-3-methylbutyl acetal, ethyl-3-methylbutyl acetal and acetaldehyde 2methylpropyl 3-methylbutyl acetal.

In certain embodiments, the at least one free carbonyl compound in the starting distilled alcoholic spirit is reduced through a conversion to a hemi-acetal. One skilled in the art would understand that a hemi-acetal includes compounds of formula: $R_x—C(OH)(OR_x)H$.

In certain embodiments, the at least one free carbonyl compound in the starting distilled alcoholic spirit is reduced through a conversion to a ketal. One skilled in the art would understand that a ketal includes compounds of formula: $R_x—C(OR_x)_2—R_x$.

In certain embodiments, the at least one free carbonyl compound in the starting distilled alcoholic spirit is reduced through a conversion to a hemi-ketal. One skilled in the art would understand that a hemi-ketal includes compounds of formula: $R_x$—C($OR_x$)(OH)—$R_x$.

Throughout the application (e.g., in the formulas above describing aldehydes, ketones, acetals, hemi-acetals, ketals and hemi-ketals), the variable $R_x$ is used to refer to a generic organic group. In one embodiment, the generic organic group has a molecular weight less than about 300 daltons, 200 daltons or 100 daltons. In certain embodiments, the generic organic group comprises between about 1-15 carbon atoms, between about 1-10 carbon atoms or between about 1-5 carbon atoms.

Certain embodiments of the invention further comprise contacting the starting distilled alcoholic spirit with a carbonyl scavenger agent.

In certain embodiments, the starting distilled alcoholic spirit is contacted with the base and the carbonyl scavenger agent simultaneously. In certain embodiments, the starting distilled alcoholic spirit is contacted with the base and the carbonyl scavenger agent sequentially. In certain embodiments, the starting distilled alcoholic spirit is contacted with the base first and with the carbonyl scavenger agent second. In certain embodiments, the starting distilled alcoholic spirit is contacted with the carbonyl scavenger agent first and base second.

Certain embodiments of the invention further comprise contacting the modified distilled alcoholic spirit with a carbonyl scavenger agent. In certain embodiments, contacting the modified distilled alcoholic spirit with the carbonyl scavenger agent causes at least one free carbonyl compound in the modified distilled alcoholic spirit to be reduced.

As used herein a carbonyl scavenger agent is a molecular entity capable of reacting with carbonyls to reduce their free form. In certain embodiments, the carbonyl scavenger agent is selected from an alcohol, a sulfite and an amine- or amide-containing molecule.

In certain embodiments, the carbonyl scavenger agent is an alcohol. As used herein an alcohol is an organic compound in which the hydroxyl functional group (—OH) is bound to a saturated carbon atom. For example, in certain embodiments, the alcohol is a polyol (i.e., alcohols containing multiple hydroxyl groups). In certain embodiments, the alcohol is trehalose.

In certain embodiments the carbonyl scavenger agent is a sulfite. As used herein a sulfite is a compound that contains the sulfite ion $SO_3^{2-}$. For example, in certain embodiments, the sulfite is sodium bisulfite.

In certain embodiments, the carbonyl scavenger agent is an amine-containing molecule. As used herein, an amine-containing molecule is an organic compound with a functional group that contains a basic nitrogen atom with a lone electron pair. Amines are derivatives of ammonia, wherein one or more hydrogens have been replaced by an alkyl or aryl group and they can be classified as primary (R—$NH_2$), secondary (R, R'—NH), tertiary (R, R', R"—N) and cyclic amines (R, R', R"—N, wherein R and R' taken with N forms a ring). As used herein, the term alkyl included both straight and branched hydrocarbon groups (e.g., a $C_1$-$C_{10}$ alkyl). It is understood that the alkyls can optionally be substituted. As used herein the term aryl includes a phenyl group (e.g., radical) and an ortho-fused bicyclic carbocyclic group (e.g., radical) having about nine to ten ring atoms in which at least one ring is aromatic. It is understood that the aryls can optionally be substituted. For example, in certain embodiments, the amine-containing molecule is an anthranilite (e.g., methyl anthranilite, ethyl anthranilite, cinnamyl anthranilite and isobutyl anthranilite). In certain embodiments, the amine-containing molecule is monosodium glutamate.

In certain embodiments, the carbonyl scavenger agent is an amide-containing molecule. As used herein, an amide-containing molecule is a small organic molecule that includes a —C(=O)N moiety. In one embodiment, the amide comprises 1-20 carbon atoms. In one embodiment, the amide comprises 1-10 carbon atoms. In certain embodiments, the amide may be cyclic or linear. For example, in certain embodiments, the amide is selected from lactamide, acetamide, 2-hydroxyethyl lactamide, 2-hydroxyethyl propionamide, N,N'-bis(2-hydroxyethyl)oxamide and butyramide. In certain embodiments, the amide is butyramide.

In certain embodiments, the carbonyl scavenger agent is a food grade additive (e.g., has GRAS status from the FDA).

In certain embodiments, the carbonyl scavenger agent is bound to a polymer (e.g., silica). In certain embodiments, the polymer bound scavenger agent is removed by, e.g., filtration. In certain embodiments, polymer bound scavenger reaction by-products (e.g., a scavenger agent bound to a carbonyl) are removed by, e.g., filtration.

In certain embodiments, the carbonyl scavenger agent is a polymer bound sulfonyl hydrazine.

In certain embodiments, the carbonyl scavenger agent is a polymer bound tosyl hydrazine.

In certain embodiments, the methods further comprise contacting the starting or modified distilled alcoholic spirit with at least one aldehyde (e.g., an aldehyde known to convert into acetal species with pleasant sensory attributes, such as positive flavor attributes). In certain embodiments, contacting the starting distilled alcoholic spirit with the at least one aldehyde results in a modified distilled alcoholic spirit with improved maturation qualities (e.g., smoothness). Such aldehydes include but are not limited to cinnamic aldehyde and vanillin, which may be converted into cinnamic aldehyde dimethyl acetal and vanillin propylene glycol acetal, respectively.

In certain embodiments, the methods further comprise contacting the starting or modified distilled alcoholic spirit with at least one ketone (e.g., a ketone known to convert into ketal species with pleasant sensory attributes, such as positive flavor attributes). In certain embodiments, contacting the starting distilled alcoholic spirit with the at least one ketone results in a modified distilled alcoholic spirit with improved maturation qualities (e.g., smoothness).

Certain embodiments of the invention further comprise contacting the modified distilled alcoholic spirit with a base (i.e., a second base, which may be the same or different from the base that is contacted with the starting distilled alcoholic spirit). In certain embodiments, contacting the modified distilled alcoholic spirit with the base causes at least one free carbonyl compound in the modified distilled alcoholic spirit to be reduced (e.g., by 10% or 20% by weight). In certain embodiments, the modified distilled alcoholic spirit is contacted with a base at least about 12 hours, 1 day, 2 days, 3 days, 4 days, 5 days, 6 days, 1 week, 2 weeks, 3 weeks or more after the starting distilled alcoholic spirit is contacted with a base. In certain embodiments, the modified distilled alcoholic spirit is contacted with a base for at least about 12 hours, 1 day, 2 days, 3 days, 4 days, 5 days, 6 days, 1 week, 2 weeks, 3 weeks or more (i.e., until the desired chemical shift has been observed, such as, e.g., at least one free carbonyl compound in the modified distilled alcoholic spirit is reduced (e.g., by about 10%)).

In certain embodiments, the at least one free carbonyl compound in the starting distilled alcoholic spirit is reduced in, e.g., two weeks (i.e., two weeks from when the starting distilled alcoholic spirit is contacted by the base). In certain embodiments, the at least one free carbonyl compound in the starting distilled alcoholic spirit is reduced in, e.g., about one week, 3 days, 1 day or 12 hours.

In certain embodiments, the at least one free carbonyl compound in the starting distilled alcoholic spirit is reduced by at least about 10% by weight in, e.g., two weeks (i.e., two weeks from when the starting distilled alcoholic spirit is contacted by the base). In certain embodiments, the at least one free carbonyl compound in the starting distilled alcoholic spirit is reduced by at least about 10% by weight in, e.g., about 1 week, 3 days, 1 day or 12 hours.

In certain embodiments, the at least one free carbonyl compound in the starting distilled alcoholic spirit is reduced by at least about 20% by weight in, e.g., two weeks (i.e., two weeks from when the starting distilled alcoholic spirit is contacted by the base). In certain embodiments, the at least one free carbonyl compound in the starting distilled alcoholic spirit is reduced by at least about 20% by weight in, e.g., about 1 week, 3 days, 1 day or 12 hours.

In certain embodiments, the total of the free carbonyl compounds in the starting distilled alcoholic spirit is reduced in, e.g., two weeks (i.e., two weeks from when the starting distilled alcoholic spirit is contacted by the base). In certain embodiments, the total of the free carbonyl compounds in the starting distilled alcoholic spirit is reduced in, e.g., about one week, 3 days, 1 day or 12 hours.

In certain embodiments, the total of the free carbonyl compounds in the starting distilled alcoholic spirit is reduced by at least about 10% by weight in, e.g., about two weeks (i.e., two weeks from when the starting distilled alcoholic spirit is contacted by the base). In certain embodiments, the total of the free carbonyl compounds in the starting distilled alcoholic spirit is reduced by at least about 10% by weight in, e.g., about 1 week, 3 days, 1 day or 12 hours.

In certain embodiments, the total of the free carbonyl compounds in the starting distilled alcoholic spirit is reduced by at least about 20% by weight in, e.g., about two weeks (i.e., two weeks from when the starting distilled alcoholic spirit is contacted by the base). In certain embodiments, the total of the free carbonyl compounds in the starting distilled alcoholic spirit is reduced by at least about 20% by weight in, e.g., about 1 week, 3 days, 1 day or 12 hours.

In certain embodiments, the trigeminal ethanol related burn, smoothness, taste, aroma and/or flavor profile of the modified distilled alcoholic spirit is improved over the starting distilled alcoholic spirit. In certain embodiments, the improvement is determined by a subject sampling the modified and starting alcoholic distilled spirits and rating them using sensory techniques such as the degree of difference test or descriptive analysis (e.g., see Examples below).

Certain embodiments of the invention provide a modified distilled alcoholic spirit prepared by the methods described herein.

Certain embodiments of the invention provide a distilled alcoholic spirit comprising less than 0.1% by weight free carbonyl compounds. In certain embodiments, the distilled alcoholic spirit comprises less than, e.g., about 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, 0.0009, 0.0008, 0.0007, 0.0006, 0.0005, 0.0004, 0.0003, 0.0002 or 0.0001% by weight free carbonyl compounds. It is to be understood that the percent by weight of free carbonyl compounds refers to the total weight of the free carbonyl compounds in the modified distilled alcoholic spirit.

For certain distilled alcoholic spirits, such as whiskey, rum and brandy, aging modifies the flavor profile. As used herein, aging refers to the period during which, after distillation and before bottling, a distilled alcoholic spirit has been stored in, e.g., oak containers. In certain embodiments, the methods of modifying a distilled alcoholic spirit as described herein may provide a maturation flavor, as the aging chemistry is accelerated (e.g., without purification processing). Accordingly, in certain embodiments, the distilled alcoholic spirit is a non-aged distilled alcoholic spirit.

Certain embodiments of the invention provide a modified distilled alcoholic spirit comprising at least one free carbonyl compound, wherein the at least one free carbonyl compound is reduced as compared to a corresponding unmodified distilled alcoholic spirit. A modified distilled alcoholic spirit is, e.g., a modified distilled alcoholic spirit prepared according to a method described herein. An unmodified distilled alcoholic spirit is, e.g., an unmodified distilled alcoholic spirit that has not been prepared according to a method described herein. In certain embodiments, the modified distilled alcoholic spirit is a non-aged modified distilled alcoholic spirit.

Certain embodiments of the invention provide a modified distilled alcoholic spirit comprising free carbonyl compounds, wherein the total of the free carbonyl compounds are reduced as compared to the total of free carbonyl compounds in a corresponding unmodified distilled alcoholic spirit. A modified distilled alcoholic spirit is, e.g., a modified distilled alcoholic spirit prepared according to a method described herein. An unmodified distilled alcoholic spirit is, e.g., an unmodified distilled alcoholic spirit that has not been prepared according to a method described herein. In certain embodiments, the modified distilled alcoholic spirit is a non-aged modified distilled alcoholic spirit.

In certain embodiments, the at least one free carbonyl compound is reduced by at least about 10, 20, 25, 30, 35, 40, 45, 50, 55, 60, 65, 70, 75, 80, 85, 90, 95, 96, 97, 98, or 99% by weight as compared to a corresponding unmodified distilled alcoholic spirit. In certain embodiments, the at least one free carbonyl compound is reduced by at least about 10% by weight as compared to a corresponding unmodified distilled alcoholic spirit. In certain embodiments, the at least one free carbonyl compound is reduced by at least about 20% by weight as compared to a corresponding unmodified distilled alcoholic spirit.

In certain embodiments, more than one free carbonyl compound is reduced.

In certain embodiments, the total of the free carbonyl compounds is reduced by at least about 10% by weight as compared to the total of free carbonyl compounds in a corresponding unmodified distilled alcoholic spirit. Accordingly, as used herein, the total weight of the free carbonyl compounds in the modified distilled alcoholic spirit must be reduced by 10% (e.g., certain free carbonyl species may be reduced while other species may be unchanged or increased). In certain embodiments, the total of the free carbonyl compounds is reduced by at least about 20% by weight as compared to the total of free carbonyl compounds in a corresponding unmodified distilled alcoholic spirit. Accordingly, as used herein, the total weight of the free carbonyl compounds in the modified distilled alcoholic spirit must be reduced by 20% (e.g., certain free carbonyl species may be reduced while other species may be unchanged or increased). In certain embodiments, the total of the free carbonyl compounds is reduced by at least about 10, 15, 20, 25, 30, 35, 40, 45, 50, 55, 60, 65, 70, 75, 80, 85, 90, 95, 96, 97, 98, or 99% by weight as compared to the total of free carbonyl compounds in a corresponding unmodified distilled alcoholic spirit.

In certain embodiments, the modified distilled alcoholic spirit has an ABV of at least about 15% (e.g., at least 20%, 30%, 40%, 45% or more) and the corresponding unmodified distilled alcoholic spirit has an ABV of at least about 15% (e.g., at least about 20%, 30%, 40%, 45% or more).

In certain embodiments, the modified distilled alcoholic spirit is whiskey. In certain embodiments, the modified distilled alcoholic spirit is rum. In certain embodiments, the modified distilled alcoholic spirit is brandy.

Certain embodiments of the invention provide a non-aged distilled alcoholic spirit with a pH greater than or equal to about 5, greater than or equal to about 6, greater than equal to about 7, greater than equal to about 8 or greater than equal to about 9.

In certain embodiments, the non-aged distilled alcoholic spirit is whiskey. In certain embodiments, the non-aged distilled alcoholic spirit is rum. In certain embodiments, the non-aged distilled alcoholic spirit is brandy.

A non-aged distilled alcoholic spirit is typically not stored for an extended period of time after distillation (e.g., in oak containers) prior to bottling. Accordingly, in certain embodiments, a non-aged distilled alcoholic spirit is not stored after distillation for longer than, e.g., about 3 months, 2 months, 1 month, 3 weeks, 2 weeks, 1 week, 6 days, 5 days, 4 days, 2 days, 1 day, 12 hours or 6 hours prior to bottling. In certain embodiments, the non-aged distilled alcoholic spirit is not stored after distillation for longer than about 4 weeks prior to bottling. In certain embodiments, the non-aged distilled alcoholic spirit is not stored after distillation prior to bottling. In contrast, an aged distilled alcoholic spirit will be stored after distillation (e.g., in oak containers) for a period of time prior to bottling. Accordingly, in certain embodiments an aged distilled alcoholic spirit will be stored after distillation (e.g., in oak containers) as designated per its standard of identity or for at least, e.g., about 4 months, 6 months, 8 months, 10 months, 1 year, 2 years, 3 years, 4 years, 5 years, 10 years, 15 years, 20 years, 25 years, 30 years, 40 years or 50 years prior to bottling.

Beer

Typically, beer refers to ale, porter, stout, or other similar fermented beverages (including saké and similar products) of any name or description containing one-half of one percent or more of alcohol by volume, brewed or produced from malt, wholly or in part, or from any substitute for malt. Beer is typically brewed from malt or from substitutes for malt, such as rice, grain of any kind, bran, glucose, sugar, and molasses. In addition, the following materials may be used as adjuncts in fermenting beer: honey, fruit, fruit juice, fruit concentrate, herbs, spices, and other such food materials. Additionally, flavors and other non-beverage ingredients containing alcohol may be used in producing beer. Generally, flavors and other non-beverage ingredients containing alcohol contribute no more than 49% of the overall alcohol content of the finished beer. (see, e.g., 27 C.F.R. § 25).

In certain embodiments, the beer has an alcohol by volume of at least about e.g., 0.5%, 1%, 2%, 3%, 4%, 5%, 6%, 7%, 8%, 9%, 10%, 11%, 12%, 13%, 14% or about 15%.

Certain embodiments of the invention provide a method of preparing a modified beer, comprising contacting a corresponding starting beer with a base under conditions that cause at least one free carbonyl compound in the starting beer to be reduced, to provide the modified beer.

Certain embodiments of the invention provide a method of preparing a modified beer, comprising contacting a corresponding starting beer with a base under conditions that cause the total of free carbonyl compounds in the starting beer to be reduced, to provide the modified beer.

In certain embodiments, the pH of the starting beer is about 2.5 to about 5 (e.g., about 3, 3.5, 4, 4.5 or 5).

In certain embodiments, the pH of the modified beer is about 3 to about 7.5 (e.g., about 3.5, 4, 4.5, 5, 5.5, 6, 6.5 or 7).

In certain embodiments, the at least one free carbonyl compound is reduced by at least about 10, 20, 25, 30, 35, 40, 45, 50, 55, 60, 65, 70, 75, 80, 85, 90, 95, 96, 97, 98, or 99% by weight. In certain embodiments, the at least one free carbonyl compound is reduced by at least about 10% by weight. In certain embodiments, the at least one free carbonyl compound is reduced by at least about 20% by weight.

In certain embodiments, more than one free carbonyl compound is reduced.

In certain embodiments, the total of the free carbonyl compounds is reduced by at least about 10% by weight. Accordingly, as used herein, the total weight of the free carbonyl compounds in the starting beer must be reduced by 10% (e.g., certain free carbonyl species may be reduced while other species may be unchanged or increased). In certain embodiments, the total of the free carbonyl compounds is reduced by at least about 20% by weight. Accordingly, as used herein, the total weight of the free carbonyl compounds in the starting beer must be reduced by 20% (e.g., certain free carbonyl species may be reduced while other species may be unchanged or increased). In certain embodiments, the total of the free carbonyl compounds is reduced by at least about 10, 15, 20, 25, 30, 35, 40, 45, 50, 55, 60, 65, 70, 75, 80, 85, 90, 95, 96, 97, 98, or 99% by weight.

In certain embodiments of the invention, the methods further comprise contacting the starting or modified beer with a carbonyl scavenger agent (e.g., as described herein).

Certain embodiments of the invention provide a modified beer prepared by the methods described herein.

Personal Hygiene Products: Mouthwash

Mouthwash generally includes liquid oral hygiene and personal care products that are variously called mouthwashes, mouth-rinses, oral antiseptics, gargles, fluoride rinses, anti-plaque rinses, and breath fresheners approved for topical application. In certain embodiments, a mouthwash does not include throat sprays or aerosol breath fresheners. Generally, basic mouthwash ingredients may include water, alcohol, cleansing agents, flavoring ingredients and/or coloring agents. Depending on the particular formulation and active ingredients, mouthwash products may be considered a drug (i.e., its intended use is for preventing or mitigating disease or to affect the structure or function of the body, e.g., by preventing cavities, removing plaque and altering appearance) or a cosmetic (see, e.g., § 201(g) of the Federal Food, Drug, and Cosmetic Act, 21 U.S.C. 321(g) and 21 C.F.R. 355).

Certain embodiments of the invention provide a method of preparing a modified mouthwash comprising providing a corresponding starting mouthwash with a pH less than about 5.5 and contacting it with a base to provide a modified mouthwash with a pH greater than about 6.

In certain embodiments, the pH of the starting mouthwash is less than about 5, is less than about 4, or is about 3.

In certain embodiments, the pH of the modified mouthwash is greater than about 6, greater than about 7, greater than about 8 or greater than about 9.

In certain embodiments, the starting mouthwash has an alcohol by volume content of at least about 5, 10, 15, 20, 25 or 30%.

In certain embodiments, at least one free carbonyl compound in the starting mouthwash is reduced by at least about 10% by weight. In certain embodiments, at least one free carbonyl compound in the starting mouthwash is reduced by at least about 20% by weight or is reduced by at least about 25, 30, 35, 40, 45, 50, 55, 60, 65, 70, 75, 80, 85, 90, 95, 96, 97, 98, or 99% by weight.

In certain embodiments more than one free carbonyl compound is reduced.

In certain embodiments, the total of the free carbonyl compounds in the starting mouthwash is reduced by at least about 10% by weight. In certain embodiments, the total of the free carbonyl compounds in the starting mouthwash is reduced by at least about 15% by weight. In certain embodiments, the total of the free carbonyl compounds in the starting mouthwash is reduced by at least about 20% by weight or is reduced by at least about 25, 30, 35, 40, 45, 50, 55, 60, 65, 70, 75, 80, 85, 90, 95, 96, 97, 98, or 99% by weight.

In certain embodiments, the at least one free carbonyl compound is an aldehyde (e.g., an aldehyde as described herein). In certain embodiments, the at least one free carbonyl compound is a ketone (e.g., a ketone as described herein).

As used herein, a base is a substance (e.g., in a solid or liquid form) that will increase the pH of the starting mouthwash. In certain embodiments, the base is a solid. In certain embodiments, the base is a food grade additive (e.g., has GRAS status from the FDA). In certain embodiments, the base is sodium bicarbonate, sodium carbonate, sodium hydroxide, potassium hydroxide, potassium carbonate or potassium bicarbonate.

In certain embodiments, the methods further comprise contacting the starting mouthwash with a carbonyl scavenger agent.

In certain embodiments, the methods further comprise contacting the modified mouthwash with a carbonyl scavenger agent. In certain embodiments, contacting the modified mouthwash with the carbonyl scavenger agent causes at least one free carbonyl compound in the modified mouthwash to be reduced.

As used herein a carbonyl scavenger agent is a molecular entity capable of reacting with carbonyls to reduce their free form. In certain embodiments, the carbonyl scavenger agent is selected from an alcohol, a sulfite and an amine- or amide-containing molecule.

In certain embodiments, the carbonyl scavenger agent is an alcohol. As used herein alcohol is an organic compound in which the hydroxyl functional group (—OH) is bound to a saturated carbon atom. For example, in certain embodiments, the alcohol is a polyol alcohols containing multiple hydroxyl groups). In certain embodiments, the alcohol is trehalose.

In certain embodiments the carbonyl scavenger agent is a sulfite. As used herein a sulfite is a compound that contains the sulfite ion $SO_3^{2-}$. For example, in certain embodiments, the sulfite is sodium bisulfate.

In certain embodiments, the carbonyl scavenger agent is an amine-containing molecule. As used herein, an amine-containing molecule is an organic compound with a functional group that contains a basic nitrogen atom with a lone electron pair. Amines are derivatives of ammonia, wherein one or more hydrogens have been replaced by an alkyl or aryl group and they can be classified as primary (R—$NH_2$), secondary (R, R'—NH), tertiary (R, R', R"—N) and cyclic amines (R, R', R"—N, wherein R and R' taken with N forms a ring). As used herein, the term alkyl included both straight and branched hydrocarbon groups (e.g., a $C_1$-$C_{10}$ alkyl). It is understood that the alkyls can optionally be substituted. As used herein the term aryl includes a phenyl group (e.g., radical) and an ortho-fused bicyclic carbocyclic group (e.g., radical) having about nine to ten ring atoms in which at least one ring is aromatic. It is understood that the aryls can optionally be substituted. For example, in certain embodiments, the amine-containing molecule is an anthranilite (e.g., methyl anthranilite). In certain embodiments, the amine-containing molecule is monosodium glutamate.

In certain embodiments, the carbonyl scavenger agent is an amide-containing molecule. As used herein, an amide-containing molecule is a small organic molecule that includes a —C(═O)N moiety. In one embodiment, the amide comprises 1-20 carbon atoms. In one embodiment, the amide comprises 1-10 carbon atoms. In certain embodiments, the amide may be cyclic or linear. For example, in certain embodiments, the amide is selected from lactamide, acetamide and butyramide. In certain embodiments, the amide is butyramide.

In certain embodiments, the carbonyl scavenger agent is a food grade additive (e.g., has GRAS status from the FDA).

In certain embodiments, the carbonyl scavenger agent is bound to a polymer (e.g., silica). In certain embodiments, the polymer bound scavenger agent is removed by, e.g., filtration. In certain embodiments, polymer bound scavenger reaction by-products (i.e., the scavenger agent bound to a carbonyl) are removed by, e.g., filtration.

In certain embodiments, the carbonyl scavenger agent is a polymer bound sulfonyl hydrazine.

In certain embodiments, the carbonyl scavenger is a polymer bound tosyl hydrazine.

In certain embodiments, the at least one free carbonyl compound in the starting mouthwash is reduced by at least about 10% by weight in, e.g., two weeks (i.e., two weeks from when the starting mouthwash is contacted by the base). In certain embodiments, the at least one free carbonyl compound in the starting mouthwash is reduced by at least about 10% by weight in, e.g., about 1 week, 6 days, 5, days, 4 days, 3 days, 2 days, 1 day, 12 hours, 6 hours, 3 hours.

In certain embodiments, the at least one free carbonyl compound in the starting mouthwash is reduced by at least about 20% by weight in, e.g., two weeks (i.e., two weeks from when the starting mouthwash is contacted by the base). In certain embodiments, the at least one free carbonyl compound in the starting mouthwash is reduced by at least about 20% by weight in, e.g., about 1 week, 6 days, 5, days, 4 days, 3 days, 2 days, 1 day, 12 hours, 6 hours, 3 hours.

In certain embodiments, the total of the free carbonyl compounds in the starting mouthwash is reduced by at least about 10% by weight in, e.g., two weeks (i.e., two weeks from when the starting mouthwash is contacted by the base). In certain embodiments, the total of the free carbonyl compounds in the starting mouthwash is reduced by at least about 10% by weight in, e.g., about 1 week, 6 days, 5 days, 4 days, 3 days, 2 days, 1 day, 12 hours or 6 hours.

In certain embodiments, the total of the free carbonyl compounds in the starting mouthwash is reduced by at least about 20% by weight in, e.g., two weeks (i.e., two weeks from when the starting mouthwash is contacted by the base). In certain embodiments, the total of the free carbonyl compounds in the starting mouthwash is reduced by at least about 20% by weight in, e.g., about 1 week, 6 days, 5 days, 4 days, 3 days, 2 days, 1 day, 12 hours or 6 hours.

In certain embodiments, the trigeminal ethanol related burn, smoothness, taste, aroma and/or flavor profile of the modified mouthwash is improved over the starting mouthwash. In certain embodiments, the improvement may be determined by a subject sampling the modified and starting mouthwashes and rating the mouthwashes using sensory techniques, such as the degree of difference test or descriptive analysis (see, e.g., the Examples).

Certain embodiments of the invention provide a modified mouthwash prepared by the methods described herein.

Certain embodiments of the invention provide a mouthwash comprising less than 0.1% by weight free carbonyl compounds. In certain embodiments, the mouthwash comprises less than, e.g., about 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, 0.0009, 0.0008, 0.0007, 0.0006, 0.0005, 0.0004, 0.0003, 0.0002 or 0.0001% by weight free carbonyl compounds. It is to be understood that the percent by weight of free carbonyl compounds refers to the total weight of the free carbonyl compounds in the mouthwash. In certain embodiments, the mouthwash has an alcohol by volume content of at least about 5, 10, 15, 20, 25 or 30%.

Certain embodiments of the invention provide a modified mouthwash (e.g., a mouthwash prepared accordingly to a method described herein, e.g., a mouthwash that has been contacted by a base) comprising at least one free carbonyl compound, wherein the at least one free carbonyl compound is reduced as compared to a corresponding unmodified mouthwash (e.g., a mouthwash that has not been prepared by a method described herein). In certain embodiments, the modified mouthwash has an alcohol by volume content of at least about 5, 10, 15, 20, 25 or 30%.

Certain embodiments of the invention provide a modified mouthwash comprising free carbonyl compounds, wherein the total of the free carbonyl compounds are reduced as compared to the total of free carbonyl compounds in a corresponding unmodified mouthwash. In certain embodiments, the modified mouthwash has an alcohol by volume content of at least about 5, 10, 15, 20, 25 or 30%.

In certain embodiments, the at least one free carbonyl compound in the modified mouthwash is reduced by at least about 10, 20, 25, 30, 35, 40, 45, 50, 55, 60, 65, 70, 75, 80, 85, 90, 95, 96, 97, 98, or 99% by weight as compared to a corresponding unmodified mouthwash. In certain embodiments, the at least one free carbonyl compound in the modified mouthwash is reduced by at least about 10% by weight as compared to a corresponding unmodified mouthwash. In certain embodiments, the at least one free carbonyl compound in the modified mouthwash is reduced by at least about 20% by weight as compared to a corresponding unmodified mouthwash.

In certain embodiments, more than one free carbonyl compound is reduced.

In certain embodiments, the total of the free carbonyl compounds in the modified mouthwash is reduced by at least about 10% by weight as compared to the total of free carbonyl compounds in a corresponding unmodified mouthwash. Accordingly, as used herein, the total weight of the free carbonyl compounds in the modified mouthwash must be reduced by 10% (e.g., certain free carbonyl species may be reduced while other species may be unchanged or increased). In certain embodiments, the total of the free carbonyl compounds in the modified mouthwash is reduced by at least about 20% by weight as compared to the total of free carbonyl compounds in a corresponding unmodified mouthwash. Accordingly, as used herein, the total weight of the free carbonyl compounds in the modified mouthwash must be reduced by 20% (e.g., certain free carbonyl species may be reduced while other species may be unchanged or increased). In certain embodiments, the total of the free carbonyl compounds is reduced by at least about 10, 15, 25, 30, 35, 40, 45, 50, 55, 60, 65, 70, 75, 80, 85, 90, 95, 96, 97, 98, or 99% by weight as compared to the total of free carbonyl compounds in the unmodified mouthwash.

Certain embodiments of the invention provide a mouthwash with a pH greater than about 6 (e.g., greater than about 6, 7, 8 or 9) and an alcohol by volume content of at least 5%. In certain embodiments, the mouthwash has improved trigeminal ethanol related burn, smoothness, taste, aroma and/or flavor profile in comparison to a corresponding mouthwash with a pH less than about 6 (e.g., less than about 6, 5.5, 5, 4.5, 4, 3.5 or 3) and an alcohol by volume content of at least 5%.

Alcohol Containing Medicaments

Certain embodiments of the invention provide a method of preparing a modified medicament comprising providing a corresponding starting medicament with a pH less than about 5 and contacting it with a base to provide a modified medicament with a pH greater than about 6, wherein the modified medicament has an alcohol by volume of at least 5%.

In certain embodiments, the pH of the starting medicament is less than about 6, is less than about 5, is less than about 4, less than about 3 or less than about 2.

In certain embodiments, the pH of the modified medicament is greater than about 6, greater than about 7, greater than about 8 or greater than about 9.

In certain embodiments, the modified medicament has an alcohol by volume content of at least about 5, 10, 15, 20, 25, 30, 35, 40 or 45%.

In certain embodiments, the starting medicament comprises at least one of a cough suppressant, an expectorant, a pain reliever, a fever reducer agent, an analgesic agent, a vasodilator agent, an antihistamine or an antispasmodic agent.

In certain embodiments, the medicament comprises a cough medicine. In certain embodiments, the medicament comprises an expectorant. In certain embodiments the medicament comprises a pain reliever and/or fever reducer. In certain embodiments, the medicament comprises an analgesic agent. In certain embodiments the medicament comprises a vasodilator. In certain embodiments the medicament comprises an antihistamine. In certain embodiments the medicament comprises an antispasmodic.

In certain embodiments, at least one free carbonyl compound in the starting medicament is reduced, e.g., is reduced by at least about 10% by weight. In certain embodiments, at least one free carbonyl compound in the starting medicament is reduced, e.g., is reduced by at least about 15% by weight. In certain embodiments, at least one free carbonyl compound in the starting medicament is reduced, e.g., is reduced by at least about 20% by weight, or at least about 25, 30, 35, 40, 45, 50, 55, 60, 65, 70, 75, 80, 85, 90, 95, 96, 97, 98, or 99% by weight. In certain embodiments, more than one free carbonyl compound is reduced.

In certain embodiments, the total of the free carbonyl compounds in the starting medicament is reduced, e.g., reduced by at least about 10% by weight. In certain embodiments, the total of the free carbonyl compounds in the starting medicament is reduced, e.g., reduced by at least about 15% by weight. In certain embodiments, the total of the free carbonyl compounds in the starting medicament is reduced, e.g., reduced by at least about 20% by weight or is reduced by at least about 25, 30, 35, 40, 45, 50, 55, 60, 65, 70, 75, 80, 85, 90, 95, 96, 97, 98, or 99% by weight.

In certain embodiments, the at least one free carbonyl compound is an aldehyde (e.g., as described herein). In certain embodiments, the at least one free carbonyl compound is a ketone.

As used herein, a base is a substance (e.g., in a solid or liquid form) that will increase the pH of the starting medicament. In certain embodiments, the base is a solid. In certain embodiments, the base is a liquid. In certain embodiments, the base is a food grade additive (e.g., has GRAS status from the FDA). In certain embodiments, the base is sodium bicarbonate, sodium carbonate, sodium hydroxide, potassium carbonate, potassium bicarbonate or potassium hydroxide.

In certain embodiments, the methods further comprise contacting the starting medicament with a carbonyl scavenger agent.

In certain embodiments, the methods further comprise contacting the modified medicament with a carbonyl scavenger agent. In certain embodiments, contacting the modified medicament with the carbonyl scavenger agent causes at least one free carbonyl compound in the modified medicament to be reduced.

As used herein a carbonyl scavenger agent is a molecular entity capable of reacting with carbonyls to reduce their free form. In certain embodiments, the carbonyl scavenger agent is selected from an alcohol, a sulfite and an amine- or amide-containing molecule.

In certain embodiments, the carbonyl scavenger agent is an alcohol. As used herein alcohol is an organic compound in which the hydroxyl functional group (—OH) is bound to a saturated carbon atom. For example, in certain embodiments, the alcohol is a polyol (i.e., alcohols containing multiple hydroxyl groups). In certain embodiments, the alcohol is trehalose.

In certain embodiments the carbonyl scavenger agent is a sulfite. As used herein a sulfite is a compound that contains the sulfite ion $SO_3^{2-}$. For example, in certain embodiments, the sulfite is sodium bisulfate.

In certain embodiments, the carbonyl scavenger agent is an amine-containing molecule. As used herein, an amine-containing molecule is an organic compound with a functional group that contains a basic nitrogen atom with a lone electron pair. Amines are derivatives of ammonia, wherein one or more hydrogens have been replaced by an alkyl or aryl group and they can be classified as primary (R—$NH_2$), secondary (R, R'—NH), tertiary (R, R', R"—N) and cyclic amines (R, R', R"—N, wherein R and R' taken with N forms a ring). As used herein, the term alkyl included both straight and branched hydrocarbon groups (e.g., a $C_1$-$C_{10}$ alkyl). It is understood that the alkyls can optionally be substituted. As used herein the term aryl includes a phenyl group (e.g., radical) and an ortho-fused bicyclic carbocyclic group (e.g., radical) having about nine to ten ring atoms in which at least one ring is aromatic. It is understood that the aryls can optionally be substituted. For example, in certain embodiments, the amine-containing molecule is an anthranilite (e.g., methyl anthranilite). In certain embodiments, the amine-containing molecule is monosodium glutamate.

In certain embodiments, the carbonyl scavenger agent is an amide-containing molecule. As used herein, an amide-containing molecule is a small organic molecule that includes a —C(=O)N moiety. In one embodiment, the amide comprises 1-20 carbon atoms. In one embodiment, the amide comprises 1-10 carbon atoms. In certain embodiments, the amide may be cyclic or linear. For example, in certain embodiments, the amide is selected from lactamide, acetamide and butyramide. In certain embodiments, the amide is butyramide.

In certain embodiments, the carbonyl scavenger agent is a food grade additive (e.g., has GRAS status from the FDA).

In certain embodiments, the carbonyl scavenger agent is bound to a polymer (e.g., silica). In certain embodiments, the polymer bound scavenger agent is removed by, e.g., filtration. In certain embodiments, polymer bound scavenger reaction by-products (e.g., scavenger agent bound to a carbonyl) are removed by, e.g., filtration.

In certain embodiments, the carbonyl scavenger agent is a polymer bound sulfonyl hydrazine.

In certain embodiments, the carbonyl scavenger is a polymer bound tosyl hydrazine.

In certain embodiments, the at least one free carbonyl compound in the starting medicament is reduced by at least about 10% by weight in, e.g., two weeks (i.e., two weeks from when the starting medicament is contacted by the base). In certain embodiments, the at least one free carbonyl compound in the starting medicament is reduced by at least about 10% by weight in, e.g., 1 week, 6 days, 5, days, 4 days, 3 days, 2 days, 1 day, 12 hours or 6 hours.

In certain embodiments, the at least one free carbonyl compound in the starting medicament is reduced by at least about 20% by weight in, e.g., two weeks (i.e., two weeks from when the starting medicament is contacted by the base). In certain embodiments, the at least one free carbonyl compound in the starting medicament is reduced by at least about 20% by weight in, e.g., 1 week, 6 days, 5, days, 4 days, 3 days, 2 days, 1 day, 12 hours or 6 hours.

In certain embodiments, the total of the free carbonyl compounds in the starting medicament is reduced by at least about 10% by weight in, e.g., about two weeks (i.e., two weeks from when the starting medicament is contacted by the base). In certain embodiments, the total of the free carbonyl compounds in the starting medicament is reduced by at least about 10% by weight in, e.g., about 1 week, 6 days, 5, days, 4 days, 3 days, 2 days, 1 day, 12 hours or 6 hours.

In certain embodiments, the total of the free carbonyl compounds in the starting medicament is reduced by at least about 20% by weight in, e.g., about two weeks (i.e., two weeks from when the starting medicament is contacted by the base). In certain embodiments, the total of the free carbonyl compounds in the starting medicament is reduced by at least about 20% by weight in, e.g., about 1 week, 6 days, 5, days, 4 days, 3 days, 2 days, 1 day, 12 hours or 6 hours.

In certain embodiments, the trigeminal ethanol related burn, smoothness, taste, aroma and/or flavor profile of the modified medicament is improved over the starting medicament. In certain embodiments, the improvement may be determined by a subject sampling the modified and starting medicaments and rating the medicaments using sensory techniques, such as the degree of difference test or descriptive analysis (see, e.g., the Examples).

Certain embodiments of the invention provide a modified medicament prepared by the methods described herein.

Certain embodiments of the invention provide a medicament comprising less than 0.1% by weight free carbonyl compounds, wherein the medicament has an alcohol by volume of at least 5%. In certain embodiments the medicament comprises less than, e.g., about 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, 0.0009, 0.0008, 0.0007, 0.0006, 0.0005, 0.0004, 0.0003, 0.0002 or 0.0001% by weight free carbonyl compounds. It is to be understood that the percent by weight of free carbonyl compounds refers to the total weight of the free carbonyl compounds in the medicament.

Certain embodiments of the invention provide a modified medicament (e.g., a medicament that has been prepared by a method described herein, e.g., a medicament that has been contacted by a base) comprising at least one free carbonyl compound, wherein the modified medicament has an alcohol by volume of at least 5%; and wherein the at least one free carbonyl compound is reduced as compared to a corresponding unmodified medicament (e.g., a medicament that has not been prepared by a method described herein).

Certain embodiments of the invention provide a modified medicament (e.g., a medicament that has been contacted by a base) comprising free carbonyl compounds, wherein the modified medicament has an alcohol by volume of at least 5%; and wherein the total of the free carbonyl compounds are reduced as compared to the total of free carbonyl compounds in a corresponding unmodified medicament.

In certain embodiments, the at least one free carbonyl compound in the modified medicament is reduced by at least about 10, 20, 25, 30, 35, 40, 45, 50, 55, 60, 65, 70, 75, 80, 85, 90, 95, 96, 97, 98, or 99% by weight as compared to a corresponding unmodified medicament. In certain embodiments, the at least one free carbonyl compound in the modified medicament is reduced by at least about 10% by weight as compared to a corresponding unmodified medicament. In certain embodiments, the at least one free carbonyl compound in the modified medicament is reduced by at least about 20% by weight as compared to a corresponding unmodified medicament.

In certain embodiments, more than one free carbonyl compound is reduced.

In certain embodiments, the total of the free carbonyl compounds in the modified medicament is reduced by at least about 10% by weight as compared to the total of free carbonyl compounds in a corresponding unmodified medicament. Accordingly, as used herein, the total weight of the free carbonyl compounds in the modified medicament are be reduced by 10% (e.g., certain free carbonyl species may be reduced while other species may be unchanged or increased). In certain embodiments, the total of the free carbonyl compounds in the modified medicament is reduced by at least about 20% by weight as compared to the total of free carbonyl compounds in a corresponding unmodified medicament. Accordingly, as used herein, the total weight of the free carbonyl compounds in the modified medicament are be reduced by 20% (e.g., certain free carbonyl species may be reduced while other species may be unchanged or increased). In certain embodiments, the total of the free carbonyl compounds is reduced by at least about 10, 15, 20, 25, 30, 35, 40, 45, 50, 55, 60, 65, 70, 75, 80, 85, 90, 95, 96, 97, 98, or 99% by weight as compared to the total of free carbonyl compounds in the unmodified medicament.

Certain embodiments of the invention provide a medicament with a pH greater than about 5 (e.g., greater than about 6, 7, 8 or 9) and an alcohol by volume content of at least 5% (e.g., at least 10%, 15%, 20% or more). In certain embodiments, the medicament has improved trigeminal ethanol related burn, smoothness, taste, aroma and/or flavor profile in comparison to a corresponding medicament with a pH less than about 5 and an alcohol by volume content of at least 5%.

In certain embodiments, the medicament comprises at least one of a cough suppressant, an expectorant, a pain reliever, a fever reducer agent, an analgesic agent, a vasodilator agent, an antihistamine or an antispasmodic agent.

The invention will now be illustrated by the following non-limiting Examples.

EXAMPLE 1

Smoothness and maturity of alcoholic beverages are general descriptors that are predominately correlated with higher palatability and consumer preference. In general, sensory changes that occur during maturation include changes in sourness, astringency, trigeminal burning sensation intensity and the mouth-feel. In general the chemical drivers of alcohol burn is not well defined.

Smoothness and maturity are desirable sensory traits and understanding the chemical drivers of those sensations may facilitate the development of ingredient or processing technologies that will allow improved palatability of a wide range of alcoholic products, including alcoholic beverages and spirits, alcohol containing personal hygiene products such as mouthwash and pharmaceutical products such as cough syrups etc. Understanding the chemical drivers of flavor perception of aqueous/ethanol systems would reveal the chemistry of smoothness and maturation perception and thus opportunities for a wide platform of alcoholic product optimization.

Most studies on alcoholic products thus far have focused on changes of volatile markers (aldehydes, ketones, esters, lactones, fusel oils etc.) during production as well as maturation-storage (depending on product) and their effect on aroma. Little is known as to how changes affect trigeminal sensation. As described herein, it has now been shown that these species undoubtedly impact the perception of trigeminal burn and consequently the smoothness and maturation.

It has been suggested that the equilibrium between aldehydes, ketones, alcohols, hemiacetals and acetals is altered in distilled spirits and alcoholic beverages (Perry, D R 1986: Whisky maturation mechanisms. In Proc. 2nd Aviemore Conf. Malt. Brew). Aldehydes have been associated with pungent, sharp aromas as well as bitterness and astringency and acetals are more pleasant and fruity (Russell I., Stewart G., Whisky: Technology, Production and Marketing 2003, Elsevier Ltd.; Perry, D R 1989: Odour intensities of whisky compounds. In Distilled Beverage flavor: Recent developments. Piggot, J R and Paterson, A. Ellis Horwood, Chichester, UK, pp 200-207) and it has been observed that their concentration can be affected by intrinsic pH of the product (during maturation) and ethanol levels.

Materials and Methods pH Modulation.

In an effort to examine the effect of pH modification on the sensory properties of aqueous/alcoholic systems a 60% water 40% ethanol solution was chosen as a representative model of distilled alcoholic beverages. The pH of that system was adjusted from 6.30 to either 3.00 or 8.00, the samples were subsequently stored for 24 hrs, and sensory and carbonyl species changes were qualitatively and quantitatively determined. The pH was adjusted with using phosphoric acid for the acidic range and sodium hydroxide for the basic range. Sensory properties of the resulted samples were examined employing a degree of difference test. The effect of the different pH modifiers on the levels of carbonyl species was also determined using the above-mentioned dynamic headspace GC/MS method.

The sensory effect of pH modification of commercially available alcoholic products was such as vodka, brandy and mouthwash was also similarly examined.

Carbonyls Species Fingerprint and Quantification.

Sample Preparation.

As a concentration step and in order to optimize our analytical method for carbonyl species quantification in aqueous-alcoholic products, sodium bisulfite was utilized as a carbonyl scavenger. Sodium bisulfite is known to react with aldehydes and ketones and form bisulfite adducts, as shown in Scheme 1, which then precipitate and are easily isolated via filtration.

Scheme 1. Reaction between sodium bisulfite and propanal resulting in the formation of bisulfite adduct.

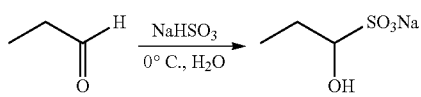

The advantage of this reaction is its reversibility, as shown in Scheme 2. Addition of a base such as sodium bicarbonate or sodium hydroxide results in regeneration of carbonyl species.

Scheme 2. Reaction between benzaldehyde and sodium bisulfite and effect of base addition.

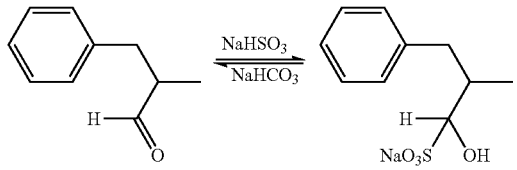

Based on this reaction scheme a method coupling carbonyl scavenging, dynamic headspace and GC/MS was developed for carbonyl species quantification. Method details can be seen in FIG. 1.

Dynamic Headspace GC/MS-Scan and SIM.

An automated dynamic headspace (DHS) method was developed for the identification and quantification of aldehydes, ketones, acetals/hemiacetals and fusel oils. Analysis was performed using a 6890 GC equipped with a 5973 Mass Selective Detector (Agilent Technologies), Thermal Desorption Unit (TDU, Gerstel), PTV inlet (CIS 4, Gerstel) and MPS 2 with headspace and DHS option (Gerstel). A highly inert CP-SIL 5CB GC column, which withstands large solvent injections, (desirable due to the high ethanol content of our samples) was used for chromatographic separation. The method was optimized and the analysis and dynamic headspace conditions are reported in Tables 1 and 2 respectively.

Aqueous samples can often be problematic for headspace analysis. The presence of water vapor in the headspace above the sample can lead to poor analytical precision. Operating the PTV inlet in solvent vent mode significantly reduced the amount of water transferred to the analytical column. The DHS system enabled dynamic purging of the headspace above a sample and trapping onto tenax TA traps, a dry purge reduced the water content. The thermal desorption tube was then placed into the Thermal Desorption Unit (TDU) and thermally desorbed into the pre-cooled CIS 4 inlet, where the analytes were cryofocused to improve peak shape before introduction into the GC column.

The mass spectrometer was operated under scan mode when sodium bisulfate was used as a concentration step.

TABLE 1

Column information and Inlet and GC oven operating parameters employed for chromatographic separation of analytes of interest.
Analysis conditions

| | |
|---|---|
| PTV | Tenax TA liner, solvent vent (60 mL/min) at 0 kPa splitless (2 min), 20° C. (0.2 min); 10° C./s; 300° C. (5 min) |
| Column | 25 m CP-SIL 5CB 0.15 mm × 2.0 μm He, constant flow = 0.5 mL/min |
| Oven | 40° C. (10 min); 10° C./min; 280° C. (6 min) |
| MSD | Scan, 28-350 amu* |

*When Mass Spectrometer was operated in scan mode

TABLE 2

Optimized dynamic headspace (DHS) and thermal desorption (TDU) flow and temperature profiles employed for trapping and injecting analytes of interest.
Dynamic headspace DHS conditions

| | |
|---|---|
| Chemical trap | Tenax TA |
| DHS | 30° C. trap temperature, 60° C. inc temperature (10 min) 50 mL purge volume, 10 mL/min purge flow 10 mL dry volume, 5 mL/min dry flow |
| TDU | solvent venting 20° C. (1 min); 720° C./min; 110° C. (1 min); 720° C./min; 300° C. (3 min) |

An optimized automated dynamic headspace (DHS) GC/MS-SIM method was also developed and employed for the analysis of alcoholic products with varying percentages of ethanol, allowing for improved sensitivity with no sample concentration step. Analysis and dynamic headspace conditions and MS SIM parameters are reported in Tables 3, 4 and 5. Briefly, 1 mL of sample (40% ethanol content) was placed in a 20 mL headspace vial and diluted with nanopure water to final volume of 10 mL. Methyl hexanoate was added as an internal standard (10 μg).

TABLE 3

Column information and Inlet and GC oven operating parameters employed for chromatographic separation of analytes of interest.
Analysis conditions

| | |
|---|---|
| PTV | Tenax TA liner, solvent vent (30 mL/min) at 0 kPa splitless (0.5 min), 20° C. (0.5 min); 10° C./s; 300° C. (5 min) |
| Column | 25 m CP-SIL 5CB 0.15 mm × 2.0 μm He, constant flow = 0.5 mL/min |
| Oven | 40° C. (10 min); 10° C./min; 280° C. (5 min) |
| MSD | SIM |

TABLE 4

Optimized dynamic headspace (DHS) and thermal desorption (TDU) flow and temperature profiles employed for trapping and injecting analytes of interest.
Dynamic headspace DHS conditions

| | |
|---|---|
| Chemical trap | Tenax TA |
| DHS | 30° C. trap temperature, 55° C. incubation temp (12 min) 2000 mL purge volume, 16 mL/min purge flow 30 mL dry volume, 7 mL/min dry flow |
| TDU | solvent venting 20° C. (0.80 min); 720° C./min; 110° C. (1 min); 720° C./min; 300° C. (4 min) |

TABLE 5

MS/single ion monitoring (SIM) parameters employed for quantification of chemical species of interest.

| Compound | m/z ions |
| --- | --- |
| Acetal | 45, 73, 103 |
| Hexanal | 56, 72, 82 |
| 2-heptanone | 58, 71, 114 |
| Heptanal | 55, 96, 114 |
| Methyl hexanoate | 74, 87, 99 |
| Benzaldehyde | 77, 105, 106 |
| Octanal | 57, 69, 84 |
| Nonanal | 57, 70, 98 |
| Decanal | 57, 95, 112 |

In order to examine and confirm as predicted that the observed differences on carbonyl species quantified (by headspace analysis) between samples with different pH values were not the result of altered volatility of the carbonyl compounds themselves (due to pH changes) 200 ml of water with pH adjusted to either 3.00 or 8.00 was spiked with 10 ppm of butanal, hexanal, heptanal, octanal, nonanal, decanal and benzaldehyde and carbonyls species were quantified via Headspace GC/MS.

Figure 2:
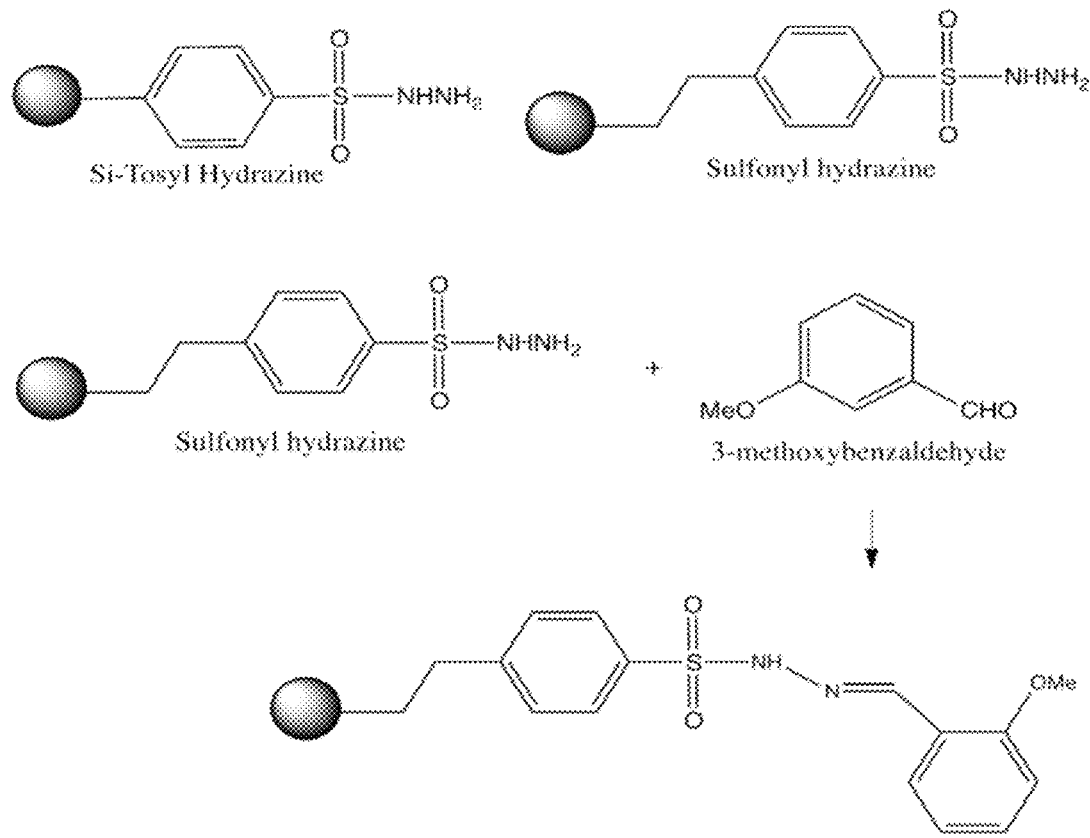
FIG. 2. Aldehyde and ketone scavenging polymer agents and trapping reaction mechanism.
Figure 3:
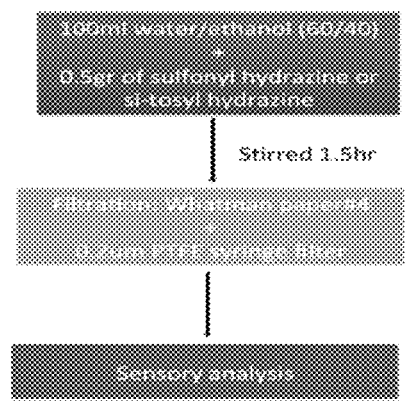
FIG. 3. Experimental protocol for carbonyl species scavenging and sensory evaluation of water/ethanol samples.

Si-Tosyl hydrazine (230-400 mesh) and sulfonyl hydrazine (30-60 mesh) with a loading capacity of 0.8 mmol/g and 1.6-3 mmol/g respectively were used. The mechanism of the trapping reaction between the polymer hydrazines and carbonyl species is presented in FIG. 2, along with the structure of the scavengers used. The experimental protocol followed for sample preparation prior to sensory analysis is illustrated in FIG. 3.

Trehalose.

Trehalose, a food grade naturally occurring disaccharide was employed due to structure reactivity towards trapping carbonyl species (presence of hydroxyl-reactive nucleophiles known to react with carbonyl species such as aldehydes and ketones). Trehalose was incorporated in relatively low levels (0.2%). Sensory evaluation was conducted after 24, 48 and 72 hrs.

Sodium Bisulfite.

Sodium bisulfite was examined as potential ingredient treatment as it reacts with carbonyl species to form adducts. It is a GRAS ingredient and it is commonly added in wine and beer to prevent yeast growth. Two levels of sodium bisulfite were utilized, namely 200 and 1000 ppm (mg/L). Employed levels were chosen based on commonly used concentration of sulfites in winemaking and were well within allowable limits (100-200 ppm of $SO_2$ in solution). Sensory evaluation was conducted after 24, 48 and 72 hrs.

Anthranilites.

This group of chemicals was explored as a potential treatment due to structure reactivity (Scheme 3) towards trapping carbonyl species (presence of amine group-reactive nucleophiles known to react with carbonyl species such as aldehydes and ketones). Methyl, ethyl, cinnamyl and isobutyl anthranilites were tested and were incorporated in relatively low levels (5 ppm). Sensory evaluation was conducted after 24, 48 and 72 hrs.

Scheme 3. From left to right: methyl anthranilite, isobutyl anthranilite.

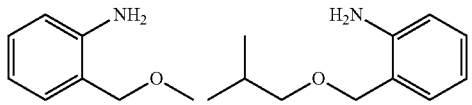

Amides.

This class of compounds was selected as a potential treatment again due the potential trapping reactivity towards carbonyl species as the amide group present can act a nucleophile and react with the electrophilic carbonyl carbon of aldehydes and ketones. The following five amide compounds were explored as potential treatments and added at levels of 50 mg/L: Lactamide, 2-hydroxyethyl lactamide, 2-hydroxyethyl propionamide, N,N'-bis(2-hydroxyethyl)oxamide and butyramide. Sensory evaluation was conducted after 24, 48 and 72 hrs.

$^1$H NMR for Analysis of Alcoholic Beverages.

Nuclear magnetic resonance (NMR) spectroscopy was used to analyzed chemical fingerprint of different vodkas and the effect of pH modification on carbonyl species in Karkov. NMR spectra collection was performed as described by Monakhova, et al., Magn. Reson. Chem., 2011, 49, 734-739. Code was developed and optimized for signal suppression of both ethanol and water and a Bruker 700 Ultrashield (5 mm TXI 700 MHz Z-Gradient). For sample preparation two buffer systems were used to accommodate the pH of vodka samples. Buffer 1 had a pH of 7.4, consisted of 1.5 M monopotassium phosphate $KH_2PO_4$ in deuterated water $D_2O$, 0.1% 3-(trimethylsilyl)-propionateacid-d4 (TSP), 3 mM Sodium Azide ($NaN_3$). Buffer 1 was utilized for sample preparation and data collection of pH modified Karkov (pH 8.00). Buffer 2 had a pH of 2.5, consisted of 1.5 M monopotassium phosphate ($KH_2PO_4$ in deuterated water $D_2O$, 0.1% 3-(trimethylsilyl)-propionateacid-d4 (TSP). Buffer 2 was utilized for sample preparation and spectra collection of original Karkov samples (pH 3.00). Data was processed and handled using TopSpin.

Sensory Analysis.

For sensory evaluation, six panelists were selected based on product usage and familiarity, discrimination ability and task comprehension. The panelists have been trained with a "smoothness" (trigeminal burn) reference scale consisting of solutions of pure food grade ethanol: nanopure water (40:60) without and with added glycerin at levels of 0.2, 0.5, 1 and 2% in order to familiarize with the sensory attributes of interest (i.e. trigeminal burn).

Degree-of-difference tests were used to estimate the difference of trigeminal burn intensity between the control samples and treated samples (pH modified and/or carbonyl scavenger treated). A 15-point linear scale was used to indicate differences in trigeminal burn of the samples ranging from no difference (0) to extremely different (15). A positive and a negative scale were used to capture both possible directional changes. A negative rating was used when the trigeminal burn intensity decreased whereas a positive value indicated an increase in trigeminal burn intensity. All samples were presented with 3-digit randomized codes at room temperature and panelists with and without nose clips during evaluation.

Three different commercial alcoholic products were included for sensory evaluation, namely vodka, brandy and mouthwash and a water/ethanol model system comprised of 60% nanopure water and 40% food grade ethanol in order to determine the sensory effect pH modification and carbonyl species in alcohol perception, smoothness and maturation. In order to further examine causality, the effect of the carbonyl concentration on smoothness (i.e. trigeminal burn) was also determined by evaluating samples with added carbonyl compounds.

Results and Discussion

Figure 4:
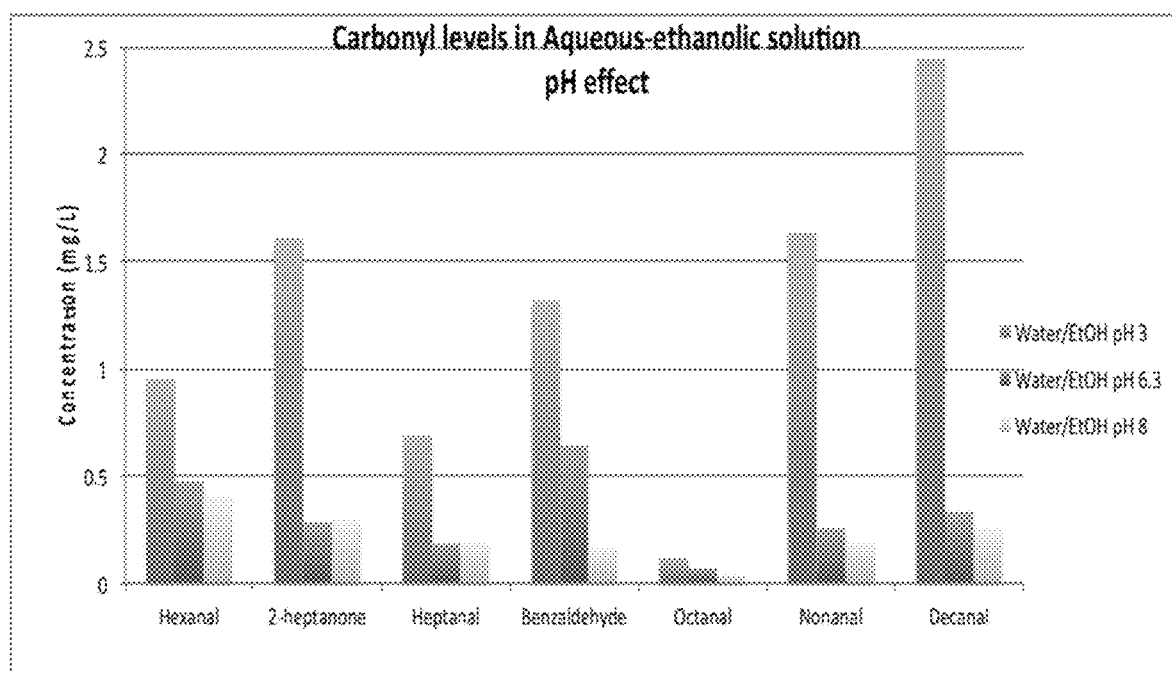
FIG. 4. Levels of carbonyl species present in water/ethanol (60/40) solutions with modified pH at 3.0, (left bar), 6.3 (middle bar) and 8.0 (right bar). Results are presented in mg/L and were obtained by DHS GC/MS FIG. 5. Levels of carbonyl species present in water/ethanol (60/40) solution (pH 6.3, left bar) and water/ethanol (60/40) solution treated with sulfonyl hydrazine (pH 6.3, right bar). Results are presented in mg/L and were obtained by DHS GC/MS.

Dynamic headspace analysis of water/ethanol (60/40) with pH 6.3 and modified pH samples at pH 3.0 and 8.0 revealed a significant difference in the content of carbonyl species. The chromatograms obtained from samples with pH 3.0 had higher numbers of aldehydes, as well as the concentrations were increased when compared to Karkov with pH 8.0. Increased pH resulted in significant reduction of aldehydes such as butanal, pentanal, hexanal, heptanal, octanal, nonanal, decanal and benzaldehyde. The observed difference between samples in content of carbonyl species was, in some cases (i.e. nonanal, decanal), upwards of 4-fold (see FIG. 4).

Sensory evaluation of these samples was also conducted in order to confirm the correlation between decreased levels of aldehydes and improved alcohol smoothness perception. Panelists were asked to rank the water/ethanol solutions with pH of 3.0, 6.3 and 8.0 utilizing a difference from control scale using water/ethanol solution with pH of 6.3 as control. Results shown in Table 6 further support the negative effect of the presence of aldehyde in smoothness perception of water/alcohol which supports our initial hypothesis and suggests that a strong correlation exists between concentration of carbonyl species in distilled spirits and flavor perception and consumer acceptability.

TABLE 6

Average (n = 6) degree of difference ratings for trigeminal burn of water/ethanol solution (60/40) with and without pH modification.

| Sample | Rating[1] |
| --- | --- |
| Water/ethanol (pH 6.3) (Blind Control) | 0.75[a] |
| Water/ethanol (pH 3.0) | 8.40[b] |
| Water/ethanol (pH 8.0) | −4.10[c] |

[1]Different letters indicate statistically significant difference determined by one-way ANOVA analysis and Dunnetts test ($\alpha = 0.05$);
[a]not significantly different than control.

Figure 5:
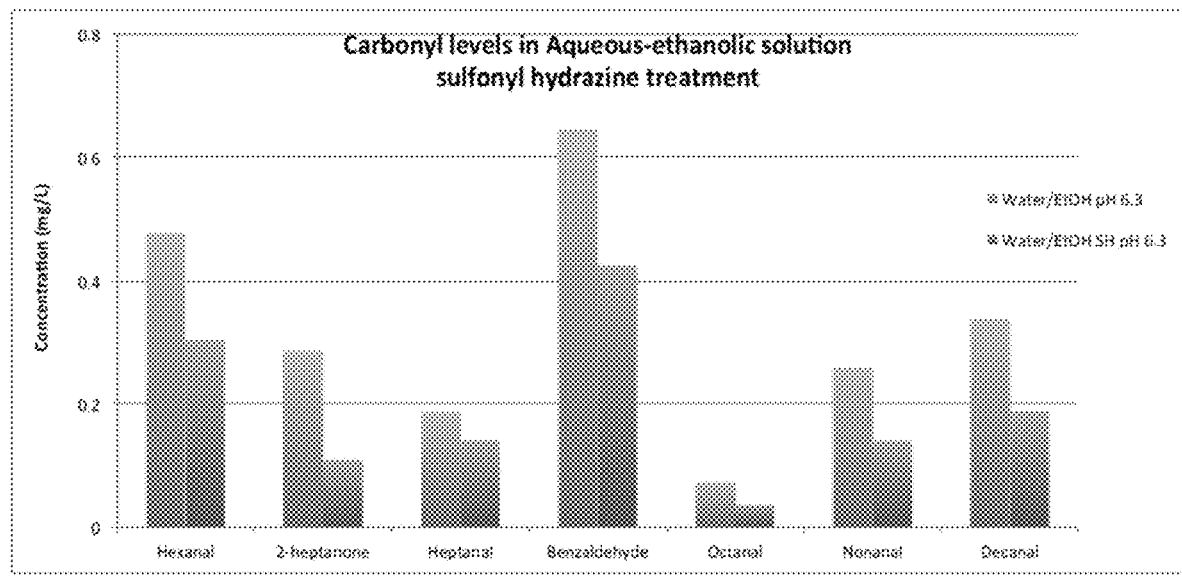

Quantification of carbonyl species of a water/ethanol solution at pH 6.3 that was treated with sulfonyl hydrazine resin (carbonyl scavenger) was performed and compared to samples with no sulfonyl hydrazine treatment and the results are presented in FIG. 5. Sulfonyl hydrazine was shown to be effective in reducing carbonyls levels as reduction after treatment ranged between 20-73%. Sensory evaluation of these samples was also conducted. Panelists were asked to rank the 2 water/ethanol samples based on increasing smoothness and the following order was revealed: Water/Ethanol pH 6.3<Water/Ethanol pH 6.3 Sulfonyl-hydrazine treated further supporting that carbonyl species appear to greatly influence smoothness, trigeminal burning sensation and the overall flavor quality of water/ethanol solution.

In order to confirm that increased amounts of aldehydes in these samples negatively affect smoothness perception and increase burn intensity, samples were prepared with higher levels of aldehydes (added 5 ppm each) and immediately the panelists were asked to rank them based on increasing smoothness: water/ethanol (pH 3.0), water/ethanol (pH 8.0), water/ethanol (pH 3.0) with spiked aldehydes (5 ppm) and water/ethanol (pH 8.0) with spiked aldehydes (5 ppm). During sensory evaluation nose clips were used as to avoid the contribution of aroma in smoothness perception and to establish the trigeminal effect of aldehydes in alcohol perception. Panelists placed the samples in the following order of increasing smoothness (lowest was on the left to highest on the right): water/ethanol (pH 3.0)+5 ppm aldehydes<water/ethanol (pH 8.0)+5 ppm aldehydes<water/ethanol (pH 3.0)<water/ethanol (pH 8.0). These results support the findings that increased concentration of aldehydes are highly influential to the flavor profile of aqueous/ethanol products, making them an important target for flavor improvement technologies. After approximately 48 hrs panelists were asked to evaluate the samples again and this time the modified water/ethanol (pH 8)+5 ppm was perceived as smoother than water/ethanol (pH 3.00) demonstrating again that pH adjustment is critical in alcohol modulation and trigeminal sensation. This also confirms that this chemistry can be potentially applied in the general platform of aqueous/ethanol products (beverages, pharmaceutical and personal hygiene) for alcohol perception modulation and improvement of sensory and organoleptic properties. The pH effects on the concentration of carbonyl species in ethanol solutions were noted to be time dependent and typically within a few hours quantitative changes in the carbonyl concentrations were observed.

Figure 6:
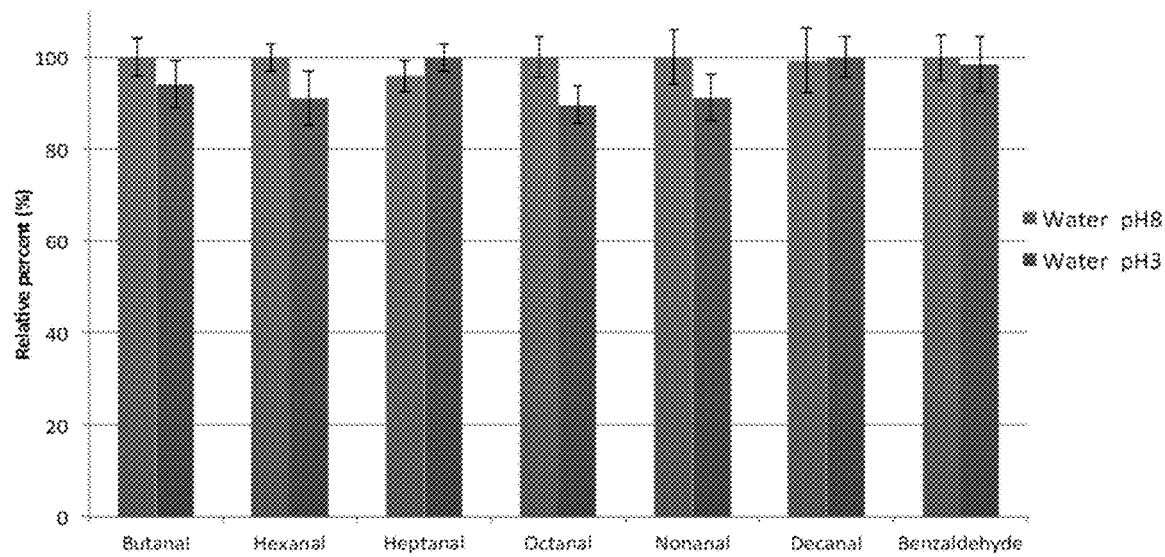
FIG. 6. Levels of carbonyl species present in water with adjusted pH 8.0 (left bar) and water with adjusted pH 3.0 (right bar) after addition of 10 ppm of butanal, hexanal, heptanal, octanal, nonanal, decanal and benzaldehyde. Results are presented in relative percent and were obtained by DHS GC/MS.

In order to confirm that the observed differences in the carbonyl load quantified between the pH modified products are not the result of a sampling error due to altered volatility at different pH values, samples consisting of either water with a pH adjusted to 8.0 or water with a pH adjusted to 3.0 and 10 ppm of butanal, hexanal, heptanal, octanal, nonanal, decanal and benzaldehyde were used. Carbonyl quantification revealed that there is no significant difference in the concentration of aldehydes between the two samples with different initial pH thus, confirming that observed differences are true and not a sample preparation artifact (FIG. 6).

Figure 7:
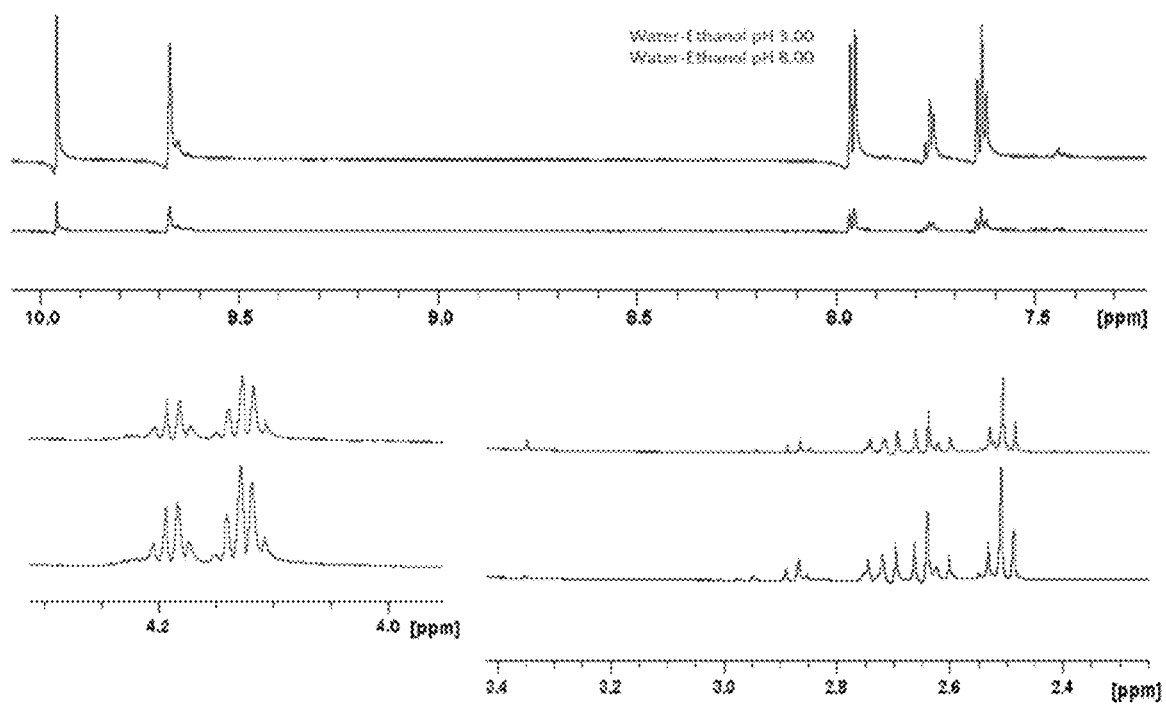
FIG. 7. Selected NMR spectra areas indicating differences between water/ethanol pH 8.0+500 ppm aldehyde solution (top line) and water/ethanol pH 3.0+500 ppm aldehyde solution (bottom line). Aldehydes added: butanal, hexanal, heptanal, octanal, nonanal, decanal and benzaldehyde.

NMR technology was also utilized to further confirm the effect of pH in the balance of carbonyl species with increasing pH favoring chemical species such as hemiacetals/acetals. We successfully applied signal suppression techniques for water and ethanol therefore increasing the signal intensity/method sensitivity of compounds found at low concentrations. In order to increase signal strength and be able to extract a more comprehensive and clearer image of the effect of pH the above mentioned aldehydes were spiked in water/ethanol solutions (40/60), at a pH 3.0 and pH 8.0 at levels of 500 ppm. The NMR spectra resulted are shown in FIG. 7.

Results visibly show chemical shifts in the characteristic aldehyde region (9.5-10.5 ppm) and there are noticeable intensity differences between the two different pH samples with the lower pH sample having significantly higher levels of aldehydes. Another important observation was the appearance of chemical shifts in the region between 3-5 ppm for the basic sample (pH 8.0) when compared to the acidic (pH 3.0) sample as chemical shifts in that region are associated with acetal-hemiacetal, lactone, lactol (cyclic equivalent of hemiacetal), ketone, ether and ester structures. These observations further support that pH modification and more specifically an increase in pH value in ethanol solutions will favor the formation of hemiacetal species and result in reduction of aldehydes which will then affect the overall flavor profile and the perceived smoothness and trigeminal burn of the product.

Based on the observed positive correlation between low carbonyl species load, high pH, and improved perceived smoothness (trigeminal sensation) we additionally exploring the sensory effects of several food grade ingredients, which can potentially act as effective carbonyl scavengers and thus be a feasible flavor improvement strategy.

Sodium bisulfite was examined due to its known carbonyl trapping ability and the fact that is a GRAS ingredient already used in wine and beer making. Two levels of sodium bisulfite 200 and 1000 ppm (mg/L) were added to the following samples: water/ethanol solution (60/40%), a commercially available vodka sample (Karkov, ethanol content 40%) and a commercially available mouthwash solution (Listerine, ethanol content 21%). The sensory properties were examined using a degree of difference test. Panelists were asked to evaluate the samples without and with a nose clip in order to examine (1) the taste/trigeminal responses alone (nose clip) and (2) taste/trigeminal with aroma (no nose clip). When panelist used nose clips and were asked to focus on smoothness and burning sensation both sodium bisulfite treated samples we perceived as smoother (Table 7) supporting the efficacy of sodium bisulfite in improving smoothness perception of vodka but when panelist were asked to comment of the overall flavor profile of vodka without using nose clips it was concluded that sodium bisulfite negatively affects the sensory properties of the products rendering it as an impractical approach for flavor improvement.

TABLE 7

Average (n = 6) degree of difference ratings for trigeminal burn of Karkov, water/ethanol solution (60/40) and Listerine mouthwash with and without sodium bisulfite. Two concentration of sodium bisulfite were used namely, 200 and 1000 ppm (mg/L).

| Sample | Rating[1] |
|---|---|
| Water/ethanol (Blind Control) | −0.50[a] |
| Water/ethanol 200 ppm SBS | −2.40[b] |
| Water/ethanol 1000 ppm SBS | −5.70[c] |
| Karkov (Blind control) | 0.70[a] |
| Karkov 200 ppm SBS | −2.70[b] |
| Karkov 1000 ppm SBS | −7.40[c] |
| Listerine (Blind control) | −0.50[a] |
| Listerine 200 ppm SBS | −3.25[b] |
| Listerine 1000 ppm SBS | −7.90[c] |

[1]Different letters indicate statistically significant difference determined by one-way ANOVA analysis and Dunnetts test ($\alpha = 0.05$);
[a]not significantly different than control.
SBS: sodium bisulfite.

Anthranilites were also examined as a potential ingredient technology for flavor improvement due to their structure reactivity towards trapping carbonyl species. The presence of amine group, which can act as a nucleophile, makes anthranilites good scavengers by reacting with the electrophilic carbonyl groups and forming adducts. Additionally anthranilites are known to have pleasant aromas such as orange blossom and grape and are approved for use as food flavorants. Methyl, ethyl, cinnamyl and isobutyl anthranilites were tested and were incorporated in relatively low levels (5 ppm) in order to maintain pleasant odor all these ingredient have relatively potent aromas. Results from the degree of difference test comparing treated samples (water/ethanol solutions and commercial vodka sample) with control and utilizing a nose clips revealed that there was no significant difference between samples regarding smoothness and burning sensation. Results could be due to the low levels incorporated (and low activity) in water/ethanol solutions and vodka. Higher levels were not investigated as their influence on the characteristic aroma profile is significant and is likely not a feasible approach for "clean" flavor profile products. The use of anthranilites, at higher levels and/or in as a mixture of compounds, could be explored in the future as a feasible treatment in different alcoholic products.

Amides were explored as potential ingredient technology due to their structure reactivity and their nucleophilicity. Five amide compounds (Lactamide, 2-hydroxyethyl lactamide, 2-hydroxyethyl propionamide, N,N'-bis(2-hydroxyethyl)oxamide, and butyramide, shown in Scheme 4) were explored as potential treatments and added at levels of 50 mg/L. Sensory properties of amide treated water/ethanol solution (60/40), Listerine mouthwash and Karkov vodka were examined employing a degree of difference test and results indicated that although smoothness-burning sensation was overall significantly improved the astringency of the samples increased resulting in an overall undesirable flavor profile. Butyramide was the only exception with no perceived increase in astringency and overall improved smoothness.

Scheme 4. Amide compounds examined for taste modulating activity and smoothness and flavor improvment of vodka.

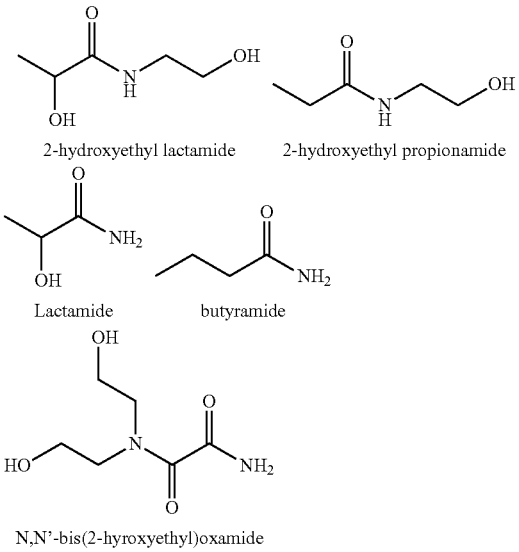

Trehalose (Scheme 5) was also examined as a potential carbonyl scavenger as well as in combination with pH modification. Trehalose is expected to be more nucleophilic under alkaline conditions and thus more reactive towards electrophilic carbonyls such as aldehydes. Additionally, trehalose has a pleasant sweet taste, is resistant to acid hydrolysis, is fairly cost effective and already has GRAS status, thus making it a suitable choice for a potential ingredient technology.

Scheme 5. Structure of natural disaccharide trehalose.

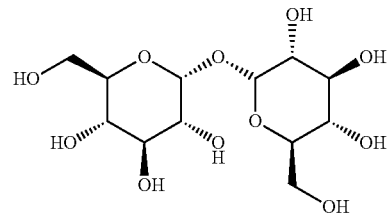

Trehalose was added (0.2% w/w) to the following samples, a water/ethanol (60/40) solution, Karkov vodka and E&J VS brandy as well as the corresponding pH modified samples. The pH modified sample of water/ethanol (60/40) solution and Karkov vodka were adjusted to 8.0 and for E&J VS brandy to 7.0. A degree-of-difference test was conducted in order to determine the trigeminal burn difference between the trehalose and/or pH modified-trehalose treated samples as compared to original samples. Overall the addition of trehalose significantly ($p<0.05$) reduced trigeminal burn perception in all tested samples (see Tables 8, 9 and 10). When trehalose addition was accompanied with pH modification the observed reduction of trigeminal burn was effective than just the pH modification alone.

TABLE 8

Average (n = 6) degree of difference ratings for trigeminal burn of Karkov vodka with and without pH modification or trehalose addition.

| Sample | Rating[1] |
|---|---|
| Karkov - Blind Control | $1.40^{a*}$ |
| Karkov trehalose | $-3.40^{b}$ |
| Karkov pH 8.0 | $-8.00^{c}$ |
| Karkov pH 8.0 trehalose | $-9.40^{d}$ |

[1]Different letters indicate statistically significant difference determined by one-way ANOVA analysis and Dunnetts test ($P < 0.05$);
[a]not significantly different than control.

TABLE 9

Average (n = 6) degree of difference ratings for trigeminal burn of water/ethanol solution (60/40) with and without pH modification or trehalose addition

| Sample | Rating[1] |
|---|---|
| Water/ethanol pH 6.3 - Blind Control | $0.60^{a*}$ |
| Water/ethanol pH 6.3-trehalose | $-2.50^{b}$ |
| Water/ethanol pH 8.0 | $-5.80^{c}$ |
| Water/ethanol pH 8.0-trehalose | $-7.75^{d}$ |

[1]Different letters indicate statistically significant difference determined by one-way ANOVA analysis and Dunnetts test ($P < 0.05$);
[a]not significantly different than control.

TABLE 10

Average (n = 6) degree of difference ratings for trigeminal burn of E&J VS brandy with and without pH modification and trehalose addition

| Sample | Rating[1] |
|---|---|
| E&J VS brandy pH 4.35 - Blind Control | $0.90^{a*}$ |
| E&J VS brandy pH 7.00 | $-5.50^{b}$ |
| E&J VS brandy pH 7.00-trehalose | $-7.00^{b}$ |

[1]Different letters indicate statistically significant difference determined by one-way ANOVA analysis and Dunnetts test ($\alpha = 0.05$);
[a]not significantly different than control.

Figure 8:
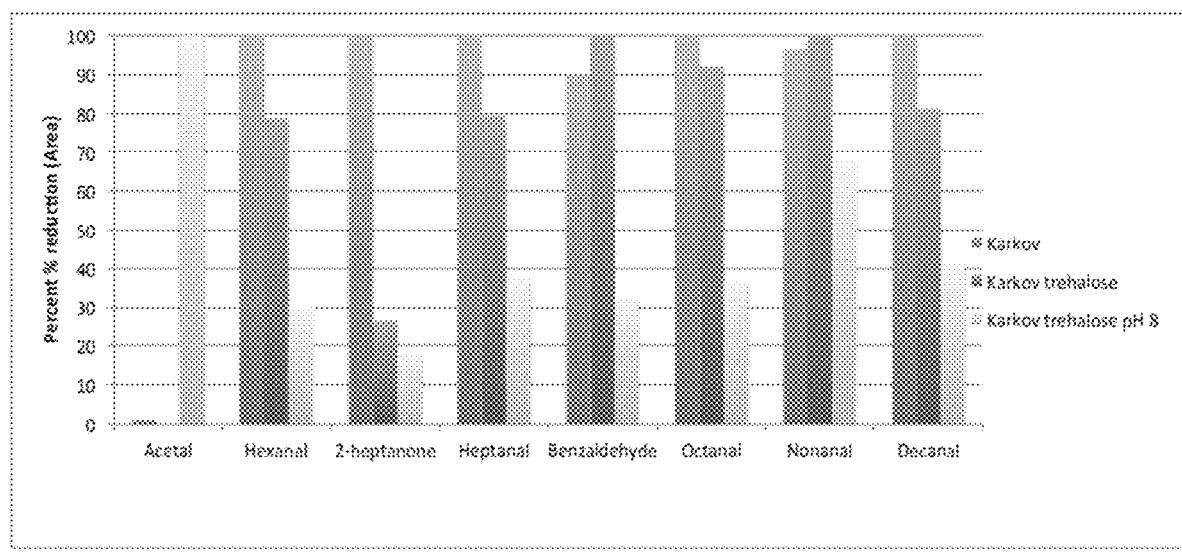
FIG. 8. Effect of trehalose on carbonyl species present in Karkov vodka. Karkov pH 3.0, (left bar), Karkov pH 3.0 trehalose (middle bar), Karkov pH 8.0 trehalose (right bar). Results are presented in area percent reduction and were obtained by DHS GC/MS-SIM. Highest peak area was adjusted to 100%.

The effect of trehalose was also analytical determined by monitoring the concentration of carbonyl species in the Karkov samples that are presented in FIG. 8. Trehalose was found to reduce the concentration of carbonyl species when compared to original Karkov vodka. The treatment of trehalose in combination with pH modification further resulted in a higher reduction of carbonyl species and a large increase in acetal species (100-fold increase of acetaldehyde diethyl acetal was reported). The analytical and sensorial data were in agreement supporting that the balance between carbonyl species and more specifically between carbonyls and their acetal/hemiacetal species affects the perceived trigeminal burn intensity and the development of the desirable maturation flavor profile. Thus, in more complex distilled products like brandy, rum and whiskey, where rich aroma and color is expected in the final product, it is possible to modulate the chemical balance via pH modification and addition of aldehydes like cinnamic aldehyde and vanillin. These aldehydes in turn could yield pleasant acetal species with sweet, spicy and fresh aroma such as cinnamaldehyde diethyl acetal or ethyl vanillin diethyl acetal and thus enhance maturation and smoothness by minimizing both trigeminal ethanol burn and reduction of astringent and bitter notes. In order to explore this concept, three samples of E&J VS original brandy were prepared, one with added aldehydes (cinnammic aldehyde and vanillin, 1 mg/L) and two with both added aldehydes and trehalose (0.2%) both with and without pH modification (pH 7.00). A difference from control sensory evaluation was used to evaluate the samples. E&J VS original with no modification or addition was used as control (and blind control) and the panelists were asked to focus on trigeminal burning sensation and maturation differences between samples and after rating to report if perceived difference was positive or negative. The results are presented in Table 11 and indicated that addition of aldehydes alone negatively impacted the alcohol smoothness and maturation (more burn intensity noted) perceived by the panelists. However when the addition of the selected aldehydes was coupled with pH modification and trehalose addition, the trigeminal burn intensity was reduced and maturation was improved as reported by panelists. Overall this product had reduced trigeminal burn and astringency and richer, slightly sweet creamier flavor profile giving the impression of a more mature brandy when compared to a control sample of E&J VS brandy. Sensory results obtained by degree of difference test are shown in Table 11.

TABLE 11

Average (n = 6) degree of difference ratings for trigeminal burn of E&J VS brandy with and without pH modification and trehalose and/or select aldehyde compound addition.

| Sample | Rating[1] |
|---|---|
| E&J VS (pH 4.35) - Blind Control | $0.90^{a*}$ |
| E&J VS (pH 4.35)-CNA-VNL | $1.70^{a}$ |
| E&J VS pH 7.00-CNA-VNL | $-8.20^{b}$ |
| E&J VS pH 7.00-CNA-VNL-trehalose | $-9.40^{b}$ |

[1]Different letters indicate statistically significant difference determined by one-way ANOVA analysis and Dunnetts test ($\alpha = 0.05$);
[a]not significantly different than control,
CNA: cinnamic aldehyde.
VNL: vanillin.

EXAMPLE 2

Introduction

Vodka is a spirit drink produced by fermentation and distillation of grain, potatoes, sugar beets, grapes, or cassava (1, 2). During vodka production, the alcohol obtained from the fermentation and distillation processes undergoes further processing such as passing through charcoal or carbon filters (see Ng, L. et al., *J. Sci. Food Agric.*, 1996, 70 (3), 380-388). The final product is obtained by blending the rectified spirit and demineralized water, which is filtered through activated carbon and deionization columns, followed by additional filtering before bottling.

The standard of identity of vodka is defined in Title 27 of the Code of Federal Regulations of Alcohol, Tobacco and Firearms Sec. 5.22 where vodka complies with the following:
 (a) Class 1; neutral spirits or alcohol. "Neutral spirits" or "alcohol" are distilled spirits produced from any material at or above 190° proof, and, if bottled, bottled at not less than 80° proof.
  (1) "Vodka" is neutral spirits so distilled, or so treated after distillation with charcoal or other materials, as to be without distinctive character, aroma, taste, or color.

Vodka accounts for nearly one-third of all distilled spirit sales and the market share has been steadily increasing for the last decade. According to the Beverage Information Group's Handbook Advance 2012, vodka sales increased by 6% from last year. This is a result of increased sales in the premium/ultra-premium price segments exhibiting a shift in consumer trends towards high quality products. The vodka market is mature, with a large number of available products, thus the best strategy for a brand to survive is to follow the current market trend and differentiate based on flavor quality.

Although vodka should be a reasonably pure mixture of alcohol and water; products typically show differences in flavor and thus consumer appeal among brands. According to FDA, the Alcohol and Tobacco Tax and Trade Bureau, as well as the EU commission, vodka can contain food grade additives such as sugar, citric acid, glycerin and food grade flavorings which of course can greatly influence the flavor profile of the spirit.

Understanding the molecular basis of vodka flavor perception provides opportunities for product optimization. The "ingredients" used for fermentation and the number of distillation and filtration steps that a product undergoes naturally determine the flavor profile of the final product. Based on the scarce available information, fuse oils and congeners compounds (fermentation products i.e. ketones, aldehydes, alcohols) are consisted to affect the overall flavor.

Phase 1

Methods

Chemical Fingerprint: Selection of High and Low Rated Products

The selection of different quality rated vodka products was performed based on consumer rating and weighted average of scores and awards from the International Wine and Spirit Competition, San Francisco World Spirits Competition, Beverage Testing Institute and Wine Enthusiast magazine (http://vodka.findthebest.com/). Twelve products that ranged widely in consumer ratings and covered the entire spectrum of vodka classifications (premium, super premium and ultra premium) were selected for the initial screening (Table 12). After an initial sensory screening, six products were selected for further investigation based on a simplify samples set and a wide range in the flavor profile. Namely Zyr, Karkov, UV, Jean-Marc XO, Luksosowa and Grey goose.

TABLE 12

| Brand | Country of origin | Base | Rating |
|---|---|---|---|
| Zyr | Russia | Winter wheat | 96 |
| UV | USA | Grain* | 87 |
| Sky 90 | USA | Wheat | 86 |
| Ketel one | Holland | Wheat | 80 |
| Jean-Marc XO | France | French wheat | 74 |
| Krystal head | Canada | Grain* | 72 |
| Grey goose | France | Wheat | 71 |
| Chopin | Poland | Potato | 71 |
| Prairie Organic | USA | Grain* | 60 |
| Gordon's | UK | Grain* | n/a |
| Luksusowa | USA | Potato | n/a |
| Karkov | USA | Grain* | 19 |

*No available information on the type of grain used for production.

The correlation between pH and flavor quality (as it related to trigeminal burn and overall smoothness) of selected vodka samples was investigated.

Materials and Methods

Measurement and Adjustments of pH

The pH of each sample was measured using a sure-flow pHe electrode specifically designed for pH measurements in high ethanol content solutions.

Sensory Evaluation/pH Effect

Two vodka samples, ZYR and Karkov (edges of the vodka quality spectrum analyzed) were selected and their pH was adjusted from 8.0 for Zyr (original) to 3.0 and from 3.0 for Karkov (original) to 8.0 using food grade phosphoric acid and sodium hydroxide respectively. Six panelists were selected based on product usage and familiarity, discrimination ability and task comprehension. The panelists have been trained with a "smoothness" (trigeminal burn) reference scale consisting of solutions of pure food grade ethanol: nanopure water (40:60) without and with added glycerin at levels of 0.2, 0.5, 1 and 2% in order to familiarize with the sensory attributes of interest (i.e. trigeminal burn).

Determination of Glycerin Concentration in Vodka Samples

Glycerol was measured according to the official method of American Oil Chemical Society (AOCS) Ea 6-51. This method can be used to determine polyalcohols containing three or more adjacent hydroxyl groups (i.e glycerol). Other polyalcohol compounds do not react at room temperature so there is extremely low possibility of interference. The reaction mechanism is shown below:

$$CH_2OH\text{—}CHOH\text{—}CH_2OH + 2NaIO_4 \rightarrow HCOOH + 2HCOH + 2NaIO_3 + H_2O$$

Formic acid (product) is used to quantify glycerol by base titration. The pH of samples was adjusted to 8.1 (indicator end point) with 0.05N sodium hydroxide solution. Blank solutions were prepared containing 40% ethanol in nanopure water with no glycerol as well as with 500 mg of glycerin to test the accuracy of the method in the presence of ethanol. All experiments were performed in duplicates. The periodate reaction occurred by adding 25 ml of sodium periodate solution while stirring. The flasks were covered with a watch glass and left standing for 30 minutes at room temperature in the dark. At the end of this period of time, 5 mL of 50% ethylene glycol solution were added to each sample and allowed to stand for another 20 minutes. The samples and the blank were titrated with sodium hydroxide solution 0.125N, using a pH meter to determine the end point, pH 6.5±0.1 for the blank, and 8.1±0.1 for the sample. The final volume used to neutralize the sample was recorded to quantify the glycerol percentage in vodka samples. The following equation was used to calculate the final glycerol concentration:

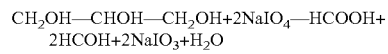

$$\text{Glycerol (wt \%)} = [(S-B) \times N \times 9.209]/W$$

where:

S=volume in mL of sodium hydroxide solution to titrate sample

B=volume in mL of sodium hydroxide solution to titrate blank

N=normality of sodium hydroxide

W=mass of sample in grams

Results and Discussion

Figure 9:
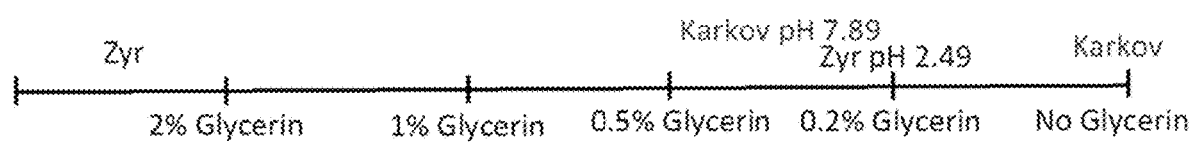
FIG. 9. Smoothness and burning sensation rating of ZYR and Karkov vodkas at different pH values. Smoothness/burning sensation was rated as compared to a standard scale constructed of different levels of glycerin in 40% ethanol solution.

The pH values of six vodka samples were determined and further compared to the quality ratings (see Table 13). The direct correlation between pH and the quality rating of these samples is apparent. The change in the noted pH of vodka samples can occur based on the extent of sample purification resulting in removal of compounds (such as acids) by absorption or distillation methods. Because of the apparent relationship between pH and flavor quality of vodka, this parameter was further investigated. The influence of pH on the taste profile of the two vodka samples, ZYR and Karkov (the edges of flavor quality spectrum) was conducted by adjusting Zyr from 8.0 to 3.0 and Karkov from 3.0 to 8.0 using food grade phosphoric acid and sodium hydroxide, respectively. These samples were presented to panelists to rate the overall trigeminal burn intensity and smoothness. A standard scale for trigeminal burn and smoothness was developed using standards consisting of 0-2% glycerin in 40% ethanol (smoothness increased with glycerin concentration) for sample comparison. The original Zyr sample at pH 8.0 was rated smoother than the 2% glycerin sample while Karkov was on the opposite end of the spectrum with high trigeminal burn (similar to 40% ethanol). When the pH of Zyr was decreased, the smoothness rating also decreased (trigeminal burn increased), while increasing the pH of Karkov similarly increased smoothness rating (trigeminal burn decreased) (FIG. 9).

TABLE 13 pH values and quality index of select vodka samples

| Vodka | pH value | Quality Index |
|---|---|---|
| Zyr | 8.0 | 90 |
| UV | 6.6 | 78 |
| Grey Goose | 6.1 | 70 |
| Jean-Marc XO | 5.7 | 73 |
| Luksusowa | 5.7 | 75 |
| Karkov | 3.0 | 39 |

Based on an observed smoothness of ZYR that was similar in comparison to the 2% glycerin standard ethanol solution, the levels of glycerin were subsequently quantified in all six vodka samples. Glycerin is a known additive to alcoholic beverages and distilled spirits, associated with smoothness and improved "body" and flavor. Only one of the tested vodka samples, Jean-Marc XO had added glycerin (at 0.18%). Thus the addition of glycerin as a flavor-modulating agent in the remaining five other vodka samples (Table 13) such as in ZYR was eliminated.

Additionally, further exploration of the effect of pH on trigeminal burn and smoothness is warranted, as a strategy for flavor improvement. The equilibrium between aldehydes, alcohols, hemiacetals and acetals in vodka and in distilled spirits is known to be affected by pH and ethanol levels typical of these products and over time of years (see Perry, D R 1986: Whisky Maturation Mechanisms. In Proc. 2nd Aviemore Conf. Malt. Brew. Distilling, (eds) Campell, I and Priest, F G. Institute of Brewing, London, pp 409-412). These products could significantly affect the overall flavor as aldehydes have been associated with pungent, sharp aromas while acetals are more pleasant and fruity (see Russell I., Stewart G., Whisky: Technology, Production and Marketing 2003, Elsevier Ltd.; and Perry, D R 1989: Odour intensities of whisky compounds. In Distilled Beverage flavor: Recent developments. Piggot, J R and Paterson, A. Ellis Horwood, Chichester, UK, pp 200-207) the effect of pH on overall aroma smoothness is demonstrated and a correlation between increased pH and increased aroma smoothness is observed.

Phase 2

Prior results described herein demonstrated a positive correlation between pH and the flavor quality of vodka. It is known that the equilibrium between aldehydes, alcohols, hemiacetals and acetals in vodka and distilled spirits are affected by pH and ethanol levels typical of these products (see Perry, D R 1986: Whisky Maturation Mechanisms. In Proc. 2nd Aviemore Conf. Malt. Brew. Distilling, (eds) Campell, I and Priest, F G. Institute of Brewing, London, pp 409-412). Consequently these products could significantly affect the overall flavor. Aldehydes have been associated with pungent, sharp aromas as well as bitterness and astringency and acetals are more pleasant and fruity (4, 5). In this phase, the focus was to characterize chemical balance between carbonyl species and fusel oils (hemiacetals/acetals) in vodka systems and related impact on the sensory properties and more specifically on trigeminal burn. Carbonyl scavengers were utilized to investigate the effect of carbonyl species on the sensory properties of vodka. Karkov and Zyr vodkas were selected for the method development and sensory evaluation as they represent the edges of the flavor quality spectrum of selected vodka products (Table 13).

Materials and Methods
Carbonyls Species Fingerprint Determination
Dynamic Headspace Analysis An automated dynamic headspace method was developed for the identification and quantification of aldehydes, ketones, acetals/hemiacetals and fusel oils. Analysis was performed using a 6890 GC equipped with a 5973 Mass Selective Detector (Agilent Technologies), Thermal Desorption Unit (TDU, Gerstel), PTV inlet (CIS 4, Gerstel) and MPS 2 with headspace and DHS option (Gerstel). A highly inert CP-SIL 5CB GC column, which withstands large solvent injections, (desirable due to the high ethanol content of our samples) was used for chromatographic separation. Method was optimized and the analysis and dynamic headspace conditions are reported in Tables 14 and 15 respectively.

TABLE 14

Column information and Inlet and GC oven operating parameters employed for chromatographic separation of analytes of interest.
Analysis conditions

| | |
|---|---|
| PTV | Tenax TA liner, solvent vent (60 mL/min) at 0 kPa splitless (2 min), 20° C. (0.2 min); 10° C./s; 300° C. (5 min) |
| Column | 25 m CP-SIL 5CB 0.15 mm × 2.0 µm He, constant flow = 0.5 mL/min |
| Oven | 40° C. (10 min); 10° C./min; 280° C. (6 min) |
| MSD | Scan, 28-350 amu |

TABLE 15

Optimized dynamic headspace (DHS) and thermal desorption (TDU) flow and temperature profiles employed for trapping and injecting analytes of interest.
Dynamic headspace DHS conditions

| | |
|---|---|
| Chemical trap | Tenax TA |
| DHS | 30° C. trap temperature, 60° C. inc temperature (10 min) 50 mL purge volume, 10 mL/min purge flow 10 mL dry volume, 5 mL/min dry flow |
| TDU | solvent venting 20° C. (1 min); 720° C./min; 110° C. (1 min); 720° C./min; 300° C. (3 min) |

Polymer-Bound Hydrazines/Carbonyl Scavengers

Figure 10:
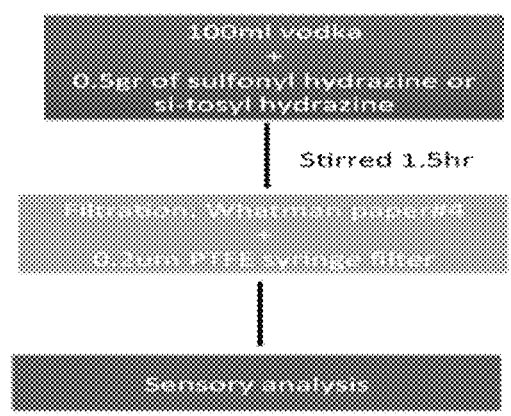
FIG. 10. Experimental protocol for carbonyl species scavenging and sensory evaluation of vodka samples.

Si-Tosyl hydrazine (230-400 mesh) and sulfonyl hydrazine (30-60 mesh) with a loading capacity of 0.8 mmol/g and 1.6-3 mmol/g respectively were used. The mechanism of the trapping reaction between the polymer hydrazines and carbonyl species is presented in FIG. 2, along with the structure of the scavengers used. The experimental protocol followed for sample preparation prior to sensory analysis is illustrated in FIG. 10.

Sensory Analysis

For sensory evaluation, six panelists were selected based on product usage and familiarity, discrimination ability and task comprehension. The panelists have been trained with a "smoothness" (trigeminal burn) reference scale consisting of solutions of pure food grade ethanol:nanopure water (40:60) without and with added glycerin at levels of 0.2, 0.5, 1 and 2% in order to familiarize with the sensory attributes of interest (i.e. trigeminal burn).

Degree-of-difference tests were used to estimate the difference of trigeminal burn intensity between the control samples and treated samples (pH modified and/or hydrazine treated). A 15-point linear scale was used to indicate differences in trigeminal burn of the samples ranging from no difference (0) to extremely different (15). A positive and a negative scale were used to capture both possible directional changes. A negative rating was used when the trigeminal burn intensity decreased whereas a positive value indicated an increase in trigeminal burn intensity. All samples were presented with 3-digit randomized codes at room temperature and panelists with and without nose clips during evaluation.

$^1$H NMR for Analysis of Alcoholic Beverages

Nuclear magnetic resonance (NMR) spectroscopy was used to analyze the chemical fingerprint of different vodkas and the effect of pH (after 24 hrs of adjustment) and hydrazine scavengers. NMR sprecta collection was performed as described by Monakhova, et al., *Magn. Reson. Chem.*, 2011, 49, 734-739. Code was developed and optimized for signal suppression of both ethanol and water and a Bruker 700 Ultrashield (5 mm TXI 700 MHz Z-Gradient). For sample preparation the buffer used was as follows: pH=7.4 (1.5 M monopotassium phosphate ($KH_2PO_4$) in deuterated water $D_2O$, 0.1% 3-(trimethylsilyl)-propionate-acid-d4 (TSP), 3 mM Sodium Azide ($NaN_3$). Data was processed and handled using TopSpin.

Results and Discussion

Figure 11:
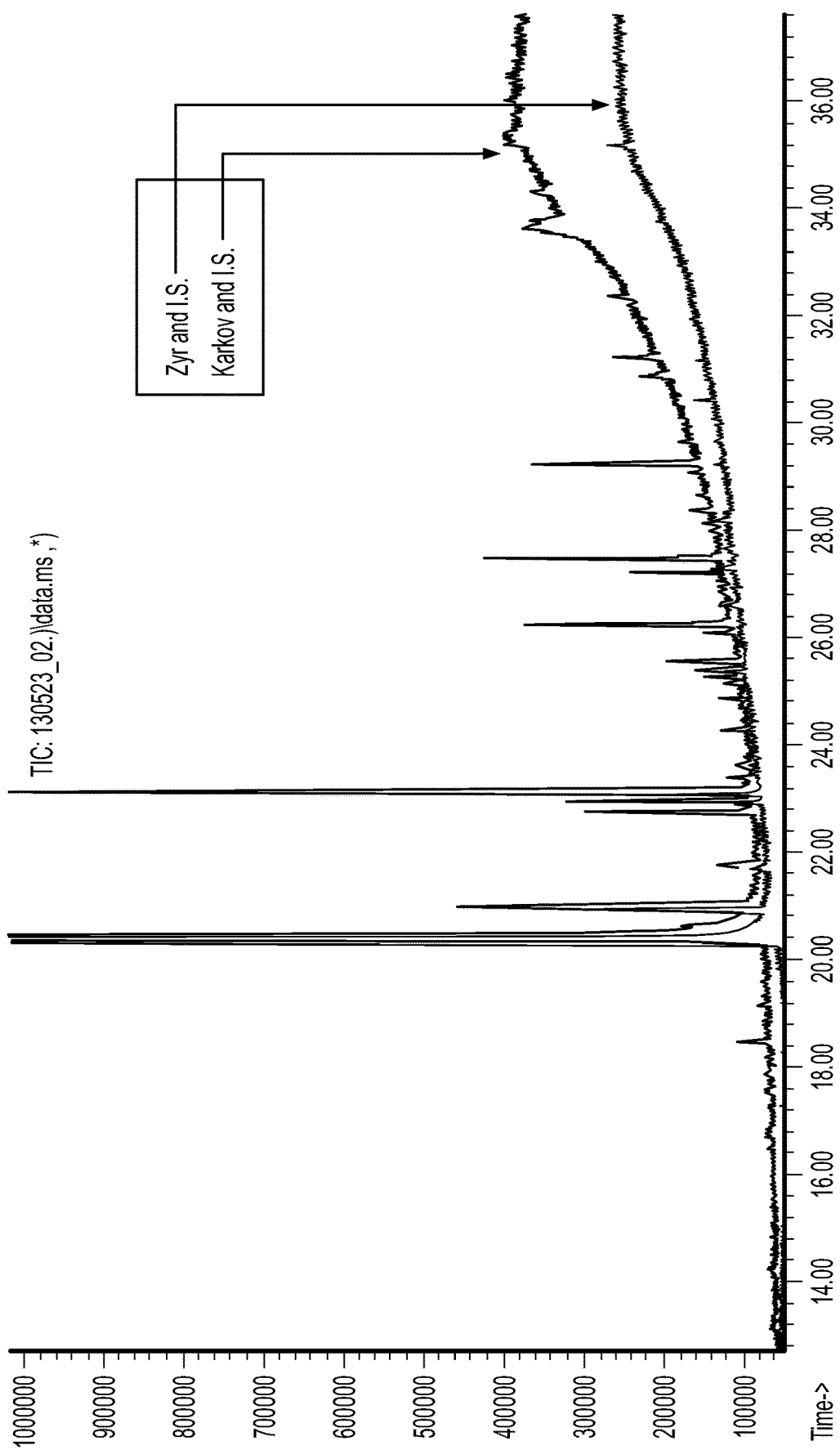
FIG. 11. Overlaid dynamic headspace chromatograms of Karkov and Zyr with internal standard from top to bottom.

Dynamic headspace analysis of Karkov (pH 3.0) and Zyr (pH 8.0) vodka samples are shown in FIG. 11. The chromatograms obtained from Karkov were more populated with aldehydes, ketones and acids as well as at higher concentrations when compared to Zyr, results shown in Table 16. The observed clear difference between Karkov (pH 3.0) and Zyr (pH 8.0) in content of carbonyl species such as aldehydes and ketones indicated a correlation between pH and the number/quantity of carbonyl compounds. Therefore pH could be affecting the balance between carbonyls and (hemi-)acetals/(hemi-)ketals and trigeminal perception and consumer acceptability.

TABLE 16

Comparison of volatile compounds identified in Zyr and Karkov.

| R.T. | Karkov | Zyr | Relative Ratio |
|---|---|---|---|
| 14.23 | acetic acid | | |
| 16.45 | isovaleraldehyde | | |
| 16.72 | 1-butanol | | |
| 18.48 | 2-butanone-3,3-dimethyl (pinacolone) | | |
| 19.18 | Acetal (ethane-1,1-diethoxy) | | |
| 19.75 | butyraldehyde | | |
| 20.89 | hexanal | hexanal | 3.1:1 |

TABLE 16-continued

Comparison of volatile compounds identified in Zyr and Karkov.

| R.T. | Karkov | Zyr | Relative Ratio |
|---|---|---|---|
| 22 | lactic acid | | |
| 23.13 | 2-heptanone | 2-heptanone | 0.85:1 |
| 23.4 | heptanal | | |
| 24.41 | 2-methyl-3-heptanone | 2-methyl-3-heptanone | 3.3:1 |
| 24.6 | | palmitaldehyde diallyl acetal | |
| 24.85 | benzaldehyde | benzaldehyde | 3.5:1 |
| 25.16 | 6-methyl-5-hepten-2-one | 6-methyl-5-hepten-2-one | 2.3:1 |
| 25.55 | octanal | octanal | 3.7:1 |
| 26.1 | 2-ethyl hexanol | 2-ethyl hexanol (emollient) | 10:1 |
| 26.99 | acetophenone | | |
| 27.21 | 2-nonanone | | |
| 27.47 | nonanal | nonanal | 7.7:1 |
| 28.13 | benzoic acid | | |
| 28.15 | | ethylhexyl acetate | |
| 28.88 | camphor | | |
| 29.22 | decanal | decanal | 17:1 |
| 30.85 | undecanal | | |

R.T.: retention time in minutes, relative ratio based on peak areas and internal standard recovery.

For example compounds such as isovaleraldehyde (herbaceous and acrid), heptanal (fatty unpleasant aroma) and undecanal (fatty, orange-like) were only present in Karkov vodka and although octanal (sharp, fatty, fruity), nonanal (fatty, orange-like) and decanal (green, fruity) were found in both Zyr and Karkov samples the later one contained significantly higher amounts (relative ratio up to 17:1).

To further evaluate the effect of carbonyl species on the flavor profile of vodka, two polymer-bound hydrazines carbonyl (carbonyl and ketone) scavenging systems were evaluated. The trigeminal burn intensity of carbonyl scavenged vodka samples were subsequently evaluated (compared to control-untreated vodka samples). The two different resins were selected based on loading capacity and efficiency namely, Si-tosyl hydrazine and sulfonyl hydrazine. Following the polymer treatment, sensory evaluation was conducted using a degree of difference test. The panelists were asked to evaluate how different the treated samples were from the control using a 15-point scale. The samples were evaluated with and without nose clips. Overall the hydrazine treated Karkov samples (Table 17) reported to have the greatest degree of difference compared to the control. The panelists reported hydrazine treated Karkov as having reduced trigeminal burn and smoother flavor with a cleaner aroma profile. Likewise hydrazine treated Zyr samples were also found to have reduced trigeminal burn, albeit the difference from control was not as large (Table 18). Overall the two different hydrazine resins used resulted in flavor improvement. Sulfonyl-hydrazine had approximately double the loading capacity of si-tosyl hydrazine and therefore it was a more efficient scavenger of carbonyl species, which correlated with the observed sensory results.

TABLE 17

Average (n = 6) degree of difference ratings for trigeminal
burn of Karkov with and without hydrazine treatments.
Two hydrazine polymers were used as carbonyl scavengers
namely, si-tosyl hydrazine and sulfonyl hydrazine.

| Sample | Rating[1] |
|---|---|
| Evaluation with nose clips | |
| Karkov (Blind Control) | 0.40[a] |
| Karkov Si-tosyl hydrazine | −5.00[b] |
| Karkov Sulfonyl hydrazine | −9.50[c] |
| Evaluation without nose clips | |
| Karkov (Blind Control) | 0.50[a] |
| Karkov Si-tosyl hydrazine | −4.50[b] |
| Karkov Sulfonyl hydrazine | −10.70[c] |

[1]different letters indicate statistically significant difference determined by one-way ANOVA analysis and Dunnetts test ($\alpha = 0.05$);
[a]not significantly different than control.

TABLE 18

Average (n = 6) degree of difference ratings for
trigeminal burn of Zyr with and without hydrazine treatments.
Two hydrazine polymers were used as carbonyl scavengers
namely, si-tosyl hydrazine and sulfonyl hydrazine.

| Sample | Rating[1] |
|---|---|
| Evaluation with nose clips | |
| Zyr (Blind Control) | −0.40[a] |
| Zyr Si-tosyl hydrazine | −2.00[b] |
| Zyr Sulfonyl hydrazine | −3.60[c] |
| Evaluation without nose clips | |
| Zyr (Blind Control) | −0.70[a] |
| Zyr Si-tosyl hydrazine | −2.00[b] |
| Zyr Sulfonyl hydrazine | −3.40[c] |

[1]different letters indicate statistically significant difference determined by one-way ANOVA analysis and Dunnetts test ($\alpha = 0.05$);
[a]not significantly different than control.

Another analytical approach utilized herein to understand vodka flavor quality was NMR technology in order to get a more comprehensive insight into the chemical fingerprint of vodka and how pH as well as scavengers, alter the chemical environment. This analytical information would help identify chemical species that impact trigeminal burn modulating activity.

Figure 12:
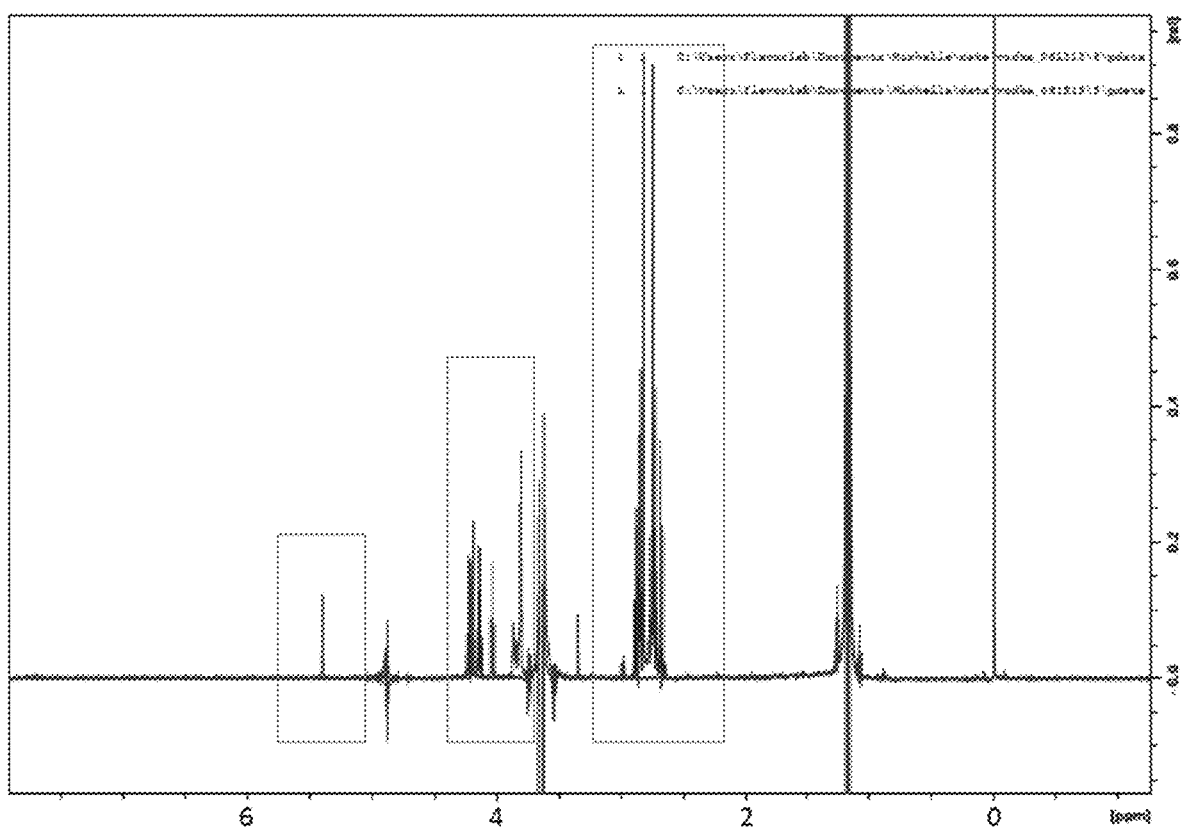
FIG. 12. Overlaid NMR spectra of Zyr and Karkov vodkas. Selected areas indicate area of differentiation between the samples.
Figure 13:
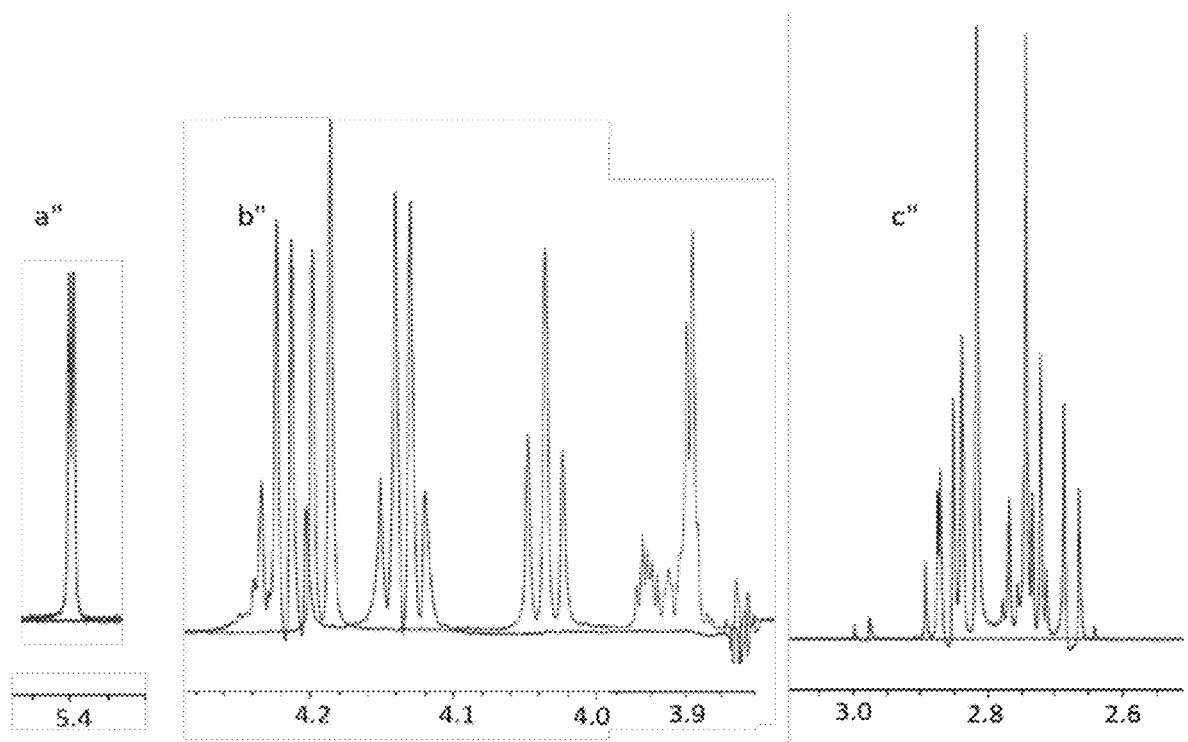
FIG. 13. Selected NMR spectra areas indicating differences between Zyr and Karkov. (a) 5.5-5.3 ppm region, (b) 4.3-3.6 ppm and (c) 3.2-2.5 ppm.

NMR analysis of alcoholic beverages can be problematic due to the presence of ethanol and water which can result in much higher intensities of NMR signals than the compounds of interest. The more attractive approach in order to overcome this hindrance is the use of suppression of undesirable NMR signals during the experiment. Preliminary experiments showed that Zyr and Karkov vodka have distinct NMR spectra (FIGS. 12 and 13).

The region between 2.8-2.7 ppm indicates the presence of alcohol or methyl hydrogen atoms neighboring an aldehyde/keto group and the signal is clearly prevailing in Karkov vodka further suggesting that presence of such carbonyl species. Signal at 3.9-3.8 ppm could be explained by the presence of hydrogen atoms neighboring ether or hydroxyl groups, more likely $CH_3$ hydrogen atoms and signals at 4.3-4.0 ppm can be associated with lactone, lactol (cyclic equivalent of hemiacetals) and acetal structures. Peaks at 5.4 ppm likely indicate $CH_2$ hydrogen atoms neighboring ether group supporting the present of acetal like molecules in Zyr vodka.

Phase 3
Introduction

Prior results described herein demonstrated a positive correlation between increased pH and the flavor quality of vodka. It has been demonstrated that there is a positive correlation between low vodka pH and increased concentration of carbonyl species that was correlated with a decreased trigeminal burn perception and smoothness. Additionally the use of carbonyl scavengers resulted in improved sensory properties further supporting that carbonyl species appear to greatly influence smoothness, burning sensation and the overall flavor profile of vodkas. In this phase of the project the focus was to quantitatively determine the concentration changes of carbonyl species in vodka systems with modified pH change and how it relates to sensory and trigeminal burn. Karkov vodka was selected for, pH modification experiments, quantitation of carbonyl species and examination of potential ingredient technologies as it represents the worst-case scenario among the initial pool of samples selected (Table 13) for this study. GC/MS and NMR technology were used to further confirm the hypothesis that pH affects the perceived trigeminal burn of vodka by influencing the balance of carbonyl species present and further demonstrate causality. In addition the quantitative data will be used for sensory re-engineering experiments. Food grade ingredients will also be investigated as potential carbonyl scavengers to be used for flavor improvement.

Materials and Methods
Carbonyls Species Fingerprint and Quantification

As a concentration step and in order to optimize the analytical method for carbonyl species quantification, sodium bisulfite was utilized as a scavenger. Sodium bisulfite is known to react with aldehydes and ketones and form bisulfite adducts as shown in Scheme 1 above, adducts then precipitate and easily isolated via filtration.

Figure 14:
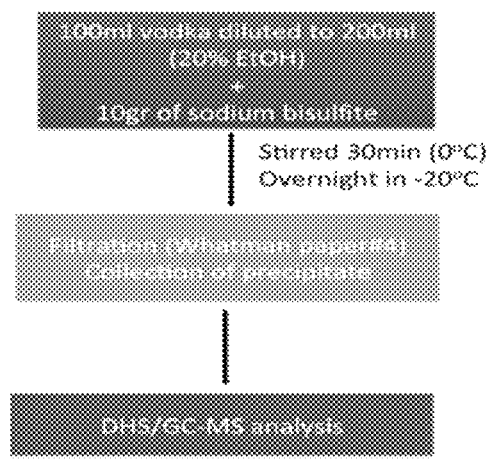
FIG. 14. Experimental protocol for carbonyl species quantification. Acetaldehyde was added as internal standard prior to trapping at levels of 5 mM.

The advantage of this reaction is its reversibility shown in Scheme 2 above. Addition of a base such as sodium bicarbonate or sodium hydroxide results in regeneration of carbonyl species. Based on this reaction scheme a method coupling carbonyl scavenging, dynamic headspace and GC/MS was developed for carbonyl species quantification. Method details can be seen in FIG. 14.

An automated dynamic headspace (DHS) method was developed for the identification and quantification of aldehydes, ketones, acetals/hemiacetals and fusel oils. Analysis was performed using a 6890 GC equipped with a 5973 Mass Selective Detector (Agilent Technologies), Thermal Desorption Unit (TDU, Gerstel), PTV inlet (CIS 4, Gerstel) and MPS 2 with headspace and DHS option (Gerstel). A highly inert CP-SIL 5CB GC column, which withstands large solvent injections, (desirable due to the high ethanol content of our samples) was used for chromatographic separation.

Figure 15:
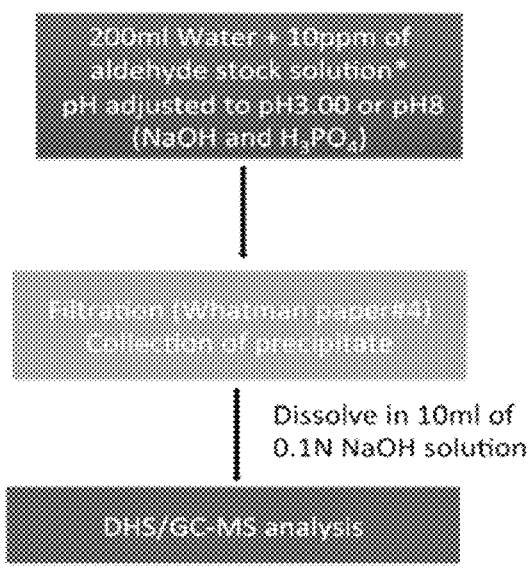
FIG. 15. Experimental protocol to test the effect of sample pH on volatility. *butanal, hexanal, heptanal, octanal, nonanal, decanal and benzaldehyde.

In order to examine and confirm (as predicted) that the observed differences on carbonyl species quantified (by headspace analysis) between samples with different pH values were not the result of altered volatility of the carbonyl compounds themselves (due to pH changes) 200 ml of water with pH adjusted to either 3.00 or 8.00 was spiked with 10 ppm of butanal, hexanal, heptanal, octanal, nonanal, decanal and benzaldehyde and carbonyls species were quantified via Headspace GC/MS. Experimental protocol used is shown in FIG. 15.

Sensory Analysis

For sensory evaluation, six panelists were selected based on product usage and familiarity, discrimination ability and task comprehension. The panelists have been trained with a "smoothness" (trigeminal burn) reference scale consisting of solutions of pure food grade ethanol: nanopure water (40:60) without and with added glycerin at levels of 0.2, 0.5, 1 and 2% in order to familiarize with the sensory attributes of interest (i.e. trigeminal burn).

Degree-of-difference tests were used to estimate the difference of trigeminal burn intensity between the control samples (Karkov) and treated samples (pH modified and/or carbonyl scavenger treated). A 15-point linear scale was used to indicate differences in trigeminal burn of the samples ranging from no difference (0) to extremely different (15). A positive and a negative scale were used to capture both possible directional changes. A negative rating was used when the trigeminal burn intensity decreased whereas a positive value indicated an increase in trigeminal burn intensity. All samples were presented with 3-digit randomized codes at room temperature and panelists with and without nose clips during evaluation.

In order to further examine causality, the effect of the carbonyl concentration on smoothness (i.e. trigeminal burn) was also determined by evaluating samples with added carbonyl compounds.

$^1$H NMR for Analysis of Alcoholic Beverages

Nuclear magnetic resonance (NMR) spectroscopy was used to analyze the chemical fingerprint of different vodkas and the effect of pH modification on carbonyl species in Karkov. NMR sprecta collection was performed as described by Monakhova, et al., *Magn. Reson. Chem.*, 2011, 49, 734-739. Code was developed and optimized for signal suppression of both ethanol and water and a Bruker 700 Ultrashield (5 mm TXI 700 MHz Z-Gradient). For sample preparation two buffer systems were used to accommodate the pH of vodka samples. Buffer 1 had a pH of 7.4, consisted of 1.5 M monopotassium phosphate ($KH_2PO_4$ in deuterated water $D_2O$, 0.1% 3-(trimethylsilyl)-propionateacid-d4 (TSP), 3 mM Sodium Azide ($NaN_3$) and was utilized for sample preparation and data collection of pH modified Karkov (pH 8.00). Buffer 2 had a pH of 2.5, consisted of 1.5 M monopotassium phosphate ($KH_2PO_4$ in deuterated water $D_2O$, 0.1% 3-(trimethylsilyl)-propionateacid-d4 (TSP) and utilized for sample preparation and spectra collection of original Karkov samples (pH 3.00). Data was processed and handled using TopSpin.

Carbonyl Scavenger Treatments

Sodium Bisulfite.

Sodium bisulfite was examined as a potential ingredient treatment as it reacts with carbonyl species to form adducts (see Schemes 1 and 2). It is a GRAS ingredient and it is commonly added in wine and beer to prevent yeast growth. Two levels of sodium bisulfite were utilized, namely 200 and 1000 ppm (mg/L) and sensory properties were examined employing a degree of difference test. Employed levels were chosen based on commonly used concentration of sulfites in winemaking and were well within allowable limits (100-200 ppm of $SO_2$ in solution). Sensory properties of the resulted samples were examined employing a degree of difference test and evaluation was conducted after 24, 48 and 72 hrs.

Anthranilites.

This group of chemicals was explored as a potential treatment due to structure reactivity (Scheme 3) towards trapping carbonyl species (presence of amine group-reactive nucleophiles known to react with carbonyl species such as aldehydes and ketones). Methyl, ethyl, cinnamyl and isobutyl anthranilites were tested and were incorporated in relatively low levels (5 ppm) and sensory properties of the resulted samples were examined employing a degree of difference test and evaluation was conducted after 24 and 72 hrs.

Amides.

This class of compounds was selected as a potential treatment due the potential trapping reactivity towards carbonyl species as the amide group present can act a nucleophile and react with the electrophilic carbonyl carbon of aldehydes and ketones. The following five amide compounds were explored as potential treatments and added at levels of 50 mg/L: Lactamide, 2-hydroxyethyl lactamide, 2-hydroxyethyl propionamide, N,N'-bis(2-hydroxyethyl)oxamide and butyramide. Sensory properties were examined employing a degree of difference test and evaluation was conducted after 24, 48 and 72 hrs.

Results and Discussion

Figure 16:
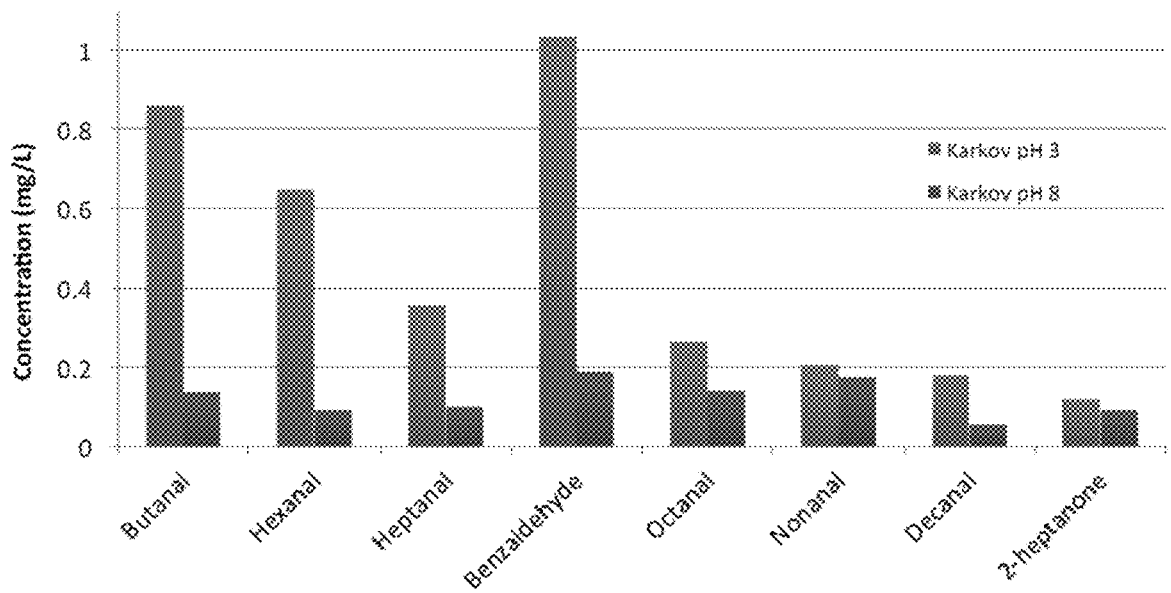
FIG. 16. Levels of carbonyl species present in Karkov vodka (pH 3.0, left bar) and modified Karkov vodka (pH 8.0, right bar). Results are presented in mg/L and were obtained by DHS GC/MS.

Dynamic headspace analysis of Karkov (pH 3.0) and modified pH Karkov vodka samples (pH 8.0) revealed significant difference in the content of carbonyl species (see, FIG. 16). The chromatograms obtained from the original Karkov vodka (pH 3.0) revealed more aldehyde species and increased concentrations when compared to pH modified Karkov (pH 8.0). Increased pH resulted in significant reduction of aldehydes such as butanal, pentanal, hexanal, heptanal, octanal, nonanal, decanal and benzaldehyde. The observed difference between Karkov (pH 3.0) and modified Karkov (pH 8.0) in content of carbonyl species was in some cases (ie. butanal, hexanal, benzaldehyde) upwards of a 80% decrease indicating a correlation between concentration of carbonyl species in distilled spirits, trigeminal burn and consumer acceptability.

Figure 17:
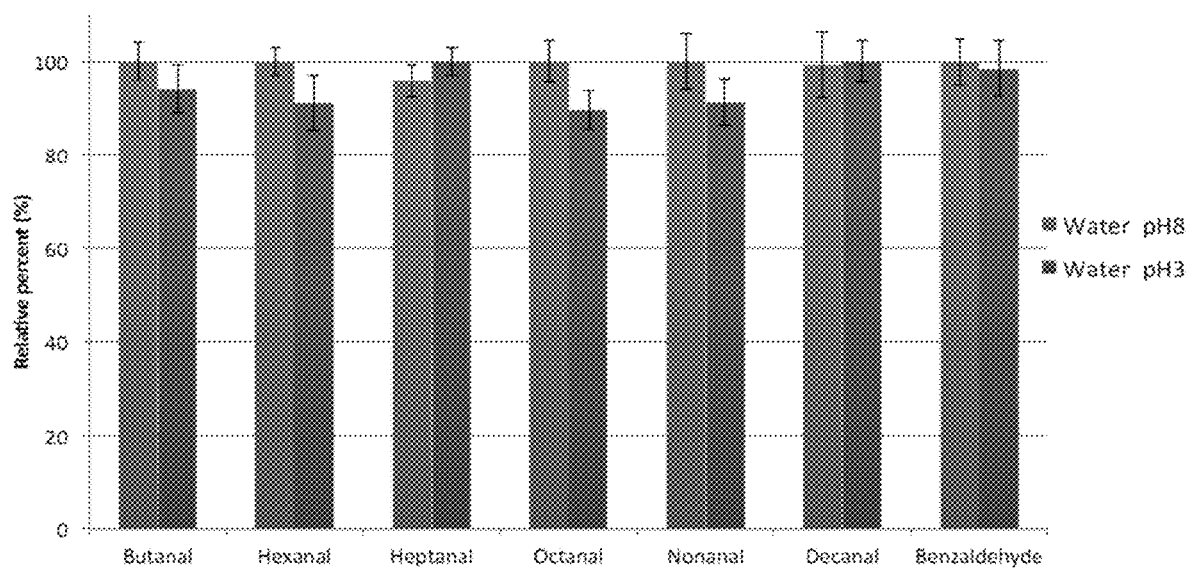
FIG. 17. Levels of carbonyl species present in water with adjusted pH 8.0 (left bar) and water with adjusted pH 3.0 (right bar) after addition of 10 ppm of butanal, hexanal, heptanal, octanal, nonanal, decanal and benzaldehyde. Results are presented in relative percent and were obtained by DHS GC/MS.

In order to confirm that the observed differences in the carbonyl load between the two vodka products is not the result of altered volatility (of the carbonyl compounds themselves) due to pH differences two samples consisting of either water with a pH adjusted to 8.0 or water with a pH adjusted to 3.0 and 10 ppm of butanal, hexanal, heptanal, octanal, nonanal, decanal and benzaldehyde were used. The same sample preparation and analytical method as described above was used for carbonyl quantification and results (FIG. 17) revealed that there is no significant difference in the concentration of aldehydes between the two samples with different initial pH.

Figure 18:
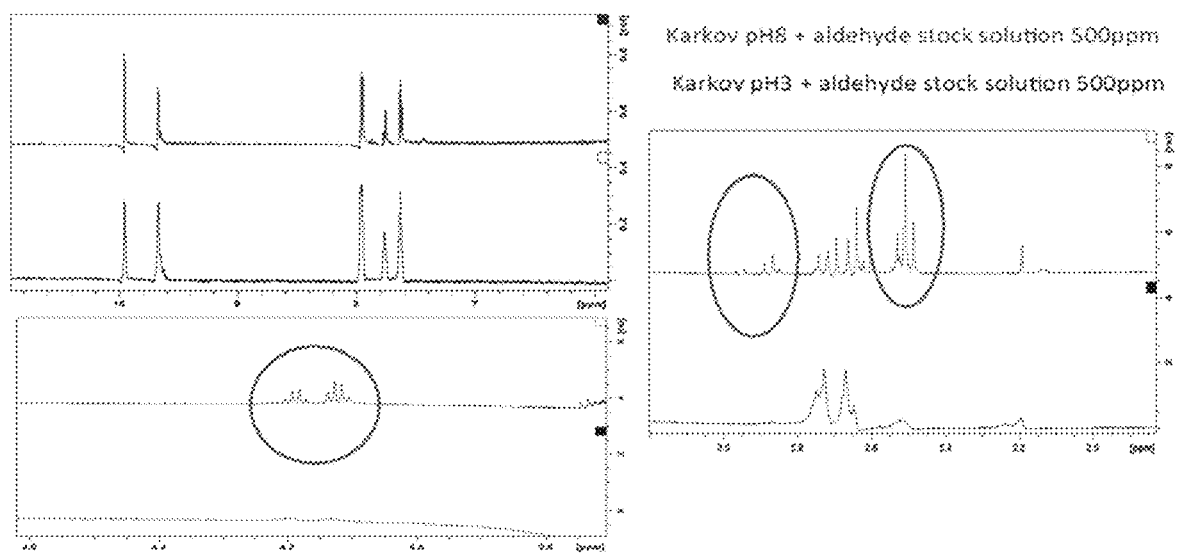
FIG. 18. Selected NMR spectra areas indicating differences between Karkov pH 8.0+500 ppm aldehyde solution (top line) and Karkov pH 3.0+500 ppm aldehyde solution (bottom line). Aldehydes added: butanal, hexanal, heptanal, octanal, nonanal, decanal and benzaldehyde.

NMR technology was also used to further confirm the effect of pH on the balance of carbonyl species and that with increasing pH chemical species such as (hemi-)acetals were favored. In order to increase signal strength and be able to extract a more comprehensive and clear image of the effect of pH the above mentioned-quantified aldehydes were spiked in Karkov (pH 3.0) and pH modified Karkov (pH 8.0) at 500 mg/L. The NMR spectra resulted are shown in FIG. 18. Results visibly show chemical shifts in the characteristic aldehyde region (9.5-10.5 ppm) and there are noticeable intensity differences between the two different pH Karkov samples with the lower pH vodka sample having significantly higher levels of aldehydes. Another significant observation was the appearance of chemical shifts in the region between 3-5 ppm for the pH modified Karkov (pH 8.0) when compared to original Karkov (pH 3.0) as chemical shifts in that region are associated with acetal-hemiacetal, lactone, lactol (cyclic equivalent of hemiacetal), ketone, ether and ester structures. These observations further support that pH modification, and more specifically an increase, favor the formation of hemiacetal species and result in reduction of aldehydes affect the overall flavor profile of vodka.

Figure 19:
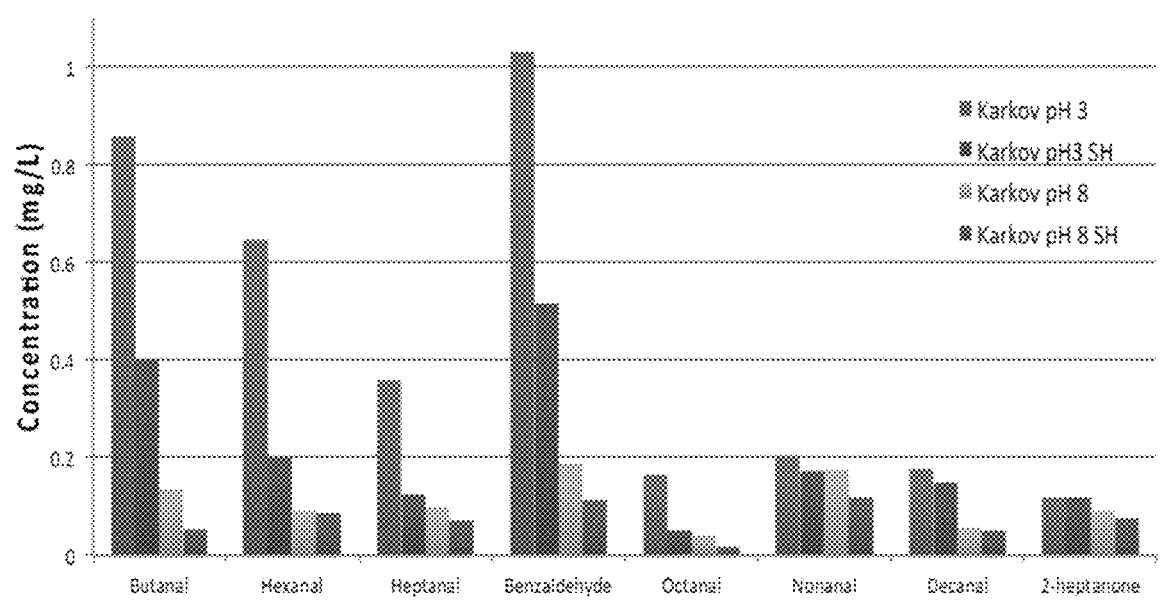
FIG. 19. Levels of carbonyl species present in the following, listed from left to right for each group: Karkov vodka (pH 3.0) and Karkov vodka (pH 3.0, treated with sulfonyl hydrazine), modified Karkov vodka (pH 8.0) and modified Karkov vodka (pH 8.0, treated with sulfonyl hydrazine). Results are presented in mg/L and were obtained by DHS GC/MS.

Quantification of carbonyl species of the two different pH Karkov samples that were additionally treated with sulfonyl hydrazine resin (carbonyl scavenger) was performed and also compared to samples with no sulfonyl hydrazine treatment; the results are shown in FIG. 19. It seems that the sulfonyl hydrazine scavenger was more effective in trapping carbonyls at pH 3.0 but that could simply be a concentration effect, as initial load of carbonyls at pH 8.0 is significantly lower. Optimization of the scavenger treatment by implementing a solid phase extraction cartridge could result in more conclusive information.

Sensory evaluation of pH modified and hydrazine treated vodka samples was conducted in order to further confirm the correlation between reduced levels of aldehydes and reduced trigeminal burn and overall improved smoothness perception. Panelists were asked to rank the samples based on increasing smoothness (lower trigeminal burn) and the following order was revealed (lowest smoothness on left, highest smoothness on right): Karkov pH 3.0<Karkov pH 3.0 SH<Karkov pH 8.0<Karkov pH 8.0 SH. These findings further supported the negative effect of higher quantities of aldehydes on smoothness and increasing the trigeminal burn perception of vodka.

It has been demonstrated that increasing pH affects the balance of carbonyl species in vodka and that correlated with smoothness. In order to confirm that increased amounts of aldehydes in these samples negatively affect smoothness perception and increase burn intensity, samples were prepared with higher levels of aldehydes (added 5 mg/L each) and immediately the panelists were asked to rank them based on increasing smoothness: Karkov (pH 3.0), modified Karkov (pH 8.0), original Karkov (pH 3.0)+5 ppm aldehydes and modified Karkov (pH 8.0)+5 ppm aldehydes. During sensory evaluation nose clips were used as to avoid the contribution of aroma in smoothness perception and to establish the trigeminal effect of aldehydes in alcohol perception. Panelists placed the samples in the following order of increasing smoothness (lowest was on the left to highest on the right): Karkov (pH 3.0)+5 ppm aldehydes<Karkov (pH 8.0)+5 ppm aldehydes<Karkov (pH 3.0)<Karkov (pH 8.0). These results further demonstrate that increased concentration of aldehydes are highly influential to the flavor profile of aqueous/ethanol products, making them an important target for flavor improvement technologies. After approximately 48 hrs panelists were asked to evaluate the samples again and this time the modified Karkov (pH 8.0)+5 ppm was perceived as smoother than original Karkov (pH 3.0) demonstrating again pH adjustment is a novel effective strategy to rapidly modify alcohol, trigeminal sensation and maturation flavor development. The pH effects on the concentration of carbonyl species in ethanol solutions were noted to be time dependent and typically within a few hours quantitative changes in the carbonyl concentrations were observed.

Based on these results, food grade ingredients, which can potentially act as effective carbonyl scavengers and thus be a feasible flavor improvement strategy, were explored.

Sodium bisulfite was examined due to its known carbonyl trapping ability and the fact that is a GRAS ingredient already used in wine and beer making. Two levels of sodium bisulfite were added in Karkov vodka, namely 200 and 1000 ppm (mg/L) and sensory properties were examined employing a degree of difference test. When panelists used nose clips and were asked to focus on smoothness and burning sensation both sodium bisulfite treated samples were perceived as smoother (Table 19) supporting the efficacy of sodium bisulfite in improving smoothness perception of vodka but when panelist were asked to comment of the overall flavor profile of vodka without using nose clips it was concluded that sodium bisulfite negatively affects the sensory properties of the product and as vodka has a very characteristic flavor profile and relatively "clean" sodium bisulfite was detectable at both levels; however, application may still possible and may work with flavored products.

TABLE 19

Average (n = 6) degree of difference ratings for trigeminal burn of Karkov, with and without sodium bisulfite. Two concentration of sodium bisulfite were used namely, 200 and 1000 ppm (mg/L).

| Sample | Rating[1] |
|---|---|
| Karkov (Blind control) | 0.70[a] |
| Karkov 200 ppm SBS | −2.70[b] |
| Karkov 1000 ppm SBS | −7.40[c] |

[1]Different letters indicate statistically significant difference determined by one-way ANOVA analysis and Dunnetts test ($\alpha = 0.05$);
[a]not significantly different than control.
SBS: sodium bisulfite.

Anthranilites were also examined as a potential ingredient technology for flavor improvement due to their structure reactivity (Scheme 3) towards trapping carbonyl species. The presence of amine group, which can act as a nucleophile, makes anthranilites good scavengers by reacting with the electrophilic carbonyl groups and forming adducts. Additionally anthranilites are known to have pleasant aromas such as orange blossom and grape and are approved for use as food flavorants. Methyl, ethyl, cinnamyl and isobutyl anthranilites were tested and were incorporated in relatively low levels (5 ppm) in order to maintain pleasant odor all these ingredient have relatively potent aromas. Results from the degree of difference test comparing treated samples with control and utilizing a nose clips revealed that there was no significant difference between samples regarding smoothness and burning sensation. Results could be due to the low levels, low activity and insufficient time tested in vodka. Higher levels were not investigated as their influence on the characteristic aroma profile is significant and is likely not a feasible approach. The use of anthranilites, at higher levels and/or in as a mixture of compounds, could be explored as a feasible treatment in flavored vodka products.

Amides were explored as potential ingredient technology due to their structure reactivity and their nucleophilicity. Five amide compounds (Lactamide, 2-hydroxyethyl lactamide, 2-hydroxyethyl propionamide, N,N'-bis(2-hydroxyethyl)oxamide, and butyramide, shown in Scheme 4) were explored as potential treatments and added at levels of 50 mg/L. Sensory properties of amide treated water/ethanol solution (60/40), Listerine mouthwash and Karkov vodka were examined employing a degree of difference test and results indicated that although smoothness-burning sensation was overall significantly improved the astringency of the samples increased resulting in an overall undesirable flavor profile. Butyramide was the only exception with no perceived increase in astringency and overall improved smoothness.

As described herein sensory re-engineering experiments will be conducted using vodka model systems aiming to identify positive and negative contributing components and determine the effect of individual aldehydes in the overall flavor profile of vodka products.

Phase 4
Introduction

In this phase of the project, optimization of the analytical methodologies was performed in order to facilitate the examination of the carbonyl fingerprint direct from vodka samples and other relevant chemical species. Alternative food grade ingredient technologies with trigeminal burn and smoothness modulating activity in combination with pH modification treatments were explored. This phase involved re-engineering experiments in order to determine the sensory effect of individual carbonyl species providing an understanding on how to design targeted ingredient technologies for flavor improvement tailored to different products.

Materials and Methods

Carbonyls Species Quantification

In order to eliminate previously employed laborious sample preparation protocol for the quantification of chemical species of interest an optimized automated dynamic headspace (DHS) method was developed and employed. Analysis was performed using a 6890 GC equipped with a 5973 Mass Selective Detector (Agilent Technologies), Thermal Desorption Unit (TDU, Gerstel), PTV inlet (CIS 4, Gerstel) and MPS 2 with headspace and DHS option (Gerstel). A highly inert CP-SIL 5CB GC column, which withstands large solvent injections (desirable due to the high ethanol content of the samples), was used for chromatographic separation.

Analysis, dynamic headspace (DHS) conditions and MS SIM parameters are reported in Tables 20, 21 and 22. No sample preparation was necessary prior to analysis. Briefly, 1 mL of sample was place in a 20 mL headspace vial and diluted with nanopure water to final volume of 10 mL. Methyl hexanoate was added as an internal standard (10 μg).

TABLE 20

Column information and Inlet and GC oven operating parameters employed for chromatographic separation of analytes of interest.
Analysis conditions

| | |
|---|---|
| PTV | Tenax TA liner, solvent vent (30 mL/min) at 0 kPa splitless (0.5 min), 20° C. (0.5 min); 10° C./s; 300° C. (5 min) |
| Column | 25 m CP-SIL 5CB 0.15 mm × 2.0 μm He, constant flow = 0.5 mL/min |
| Oven | 40° C. (10 min); 10° C./min; 280° C. (5 min) |
| MSD | SIM |

TABLE 21

Optimized dynamic headspace (DHS) and thermal desorption (TDU) flow and temperature profiles employed for trapping and injecting analytes of interest.
Dynamic headspace DHS conditions

| | |
|---|---|
| Chemical trap | Tenax TA |
| DHS | 30° C. trap temperature, 55° C. incubation temp (12 min) 2000 mL purge volume, 16 mL/min purge flow 30 mL dry volume, 7 mL/min dry flow |
| TDU | solvent venting 20° C. (0.80 min); 720° C./min; 110° C. (1 min); 720° C./min; 300° C. (4 min) |

TABLE 22

MS/single ion monitoring parameters employed for quantification of chemical species of interest.

| Compound | m/z ions |
|---|---|
| Acetal | 45, 73, 103 |
| Hexanal | 56, 72, 82 |
| 2-heptanone | 58, 71, 114 |
| Heptanal | 55, 96, 114 |
| Methyl hexanoate | 74, 87, 99 |
| Benzaldehyde | 77, 105, 106 |

TABLE 22-continued

MS/single ion monitoring parameters employed for quantification of chemical species of interest.

| Compound | m/z ions |
|---|---|
| Octanal | 57, 69, 84 |
| Nonanal | 57, 70, 98 |
| Decanal | 57, 95, 112 |

Sensory Analysis

For sensory evaluation, six panelists were selected based on product usage and familiarity, discrimination ability and task comprehension. The panelists have been trained with a "smoothness" (trigeminal burn) reference scale consisting of solutions of pure food grade ethanol: nanopure water (40:60) without and with added glycerin at levels of 0.2, 0.5, 1 and 2% in order to familiarize with the sensory attributes of interest (i.e. trigeminal burn).

Degree-of-difference tests were used to estimate the difference of trigeminal burn intensity between the control samples (Karkov) and treated samples (pH modified and/or carbonyl scavenger treated). A 15-point linear scale was used to indicate differences in trigeminal burn of the samples ranging from no difference (0) to extremely different (15). A positive and a negative scale were used to capture both possible directional changes. A negative rating was used when the trigeminal burn intensity decreased whereas a positive value indicated an increase in trigeminal burn intensity. All samples were presented with 3-digit randomized codes at room temperature and panelists with and without nose clips during evaluation.

pH Modulating Agents

To investigate the sensorial effect of different pH modifiers, food grade sodium bicarbonate and sodium carbonate was examined and compared to food grade sodium hydroxide, which has been used thus far. Sodium carbonate, sodium bicarbonate and sodium hydroxide were incorporated in samples to achieve a pH of 8.00±0.05, 7.65±0.05 and 8.00±0.05 respectively. Sensory properties of the pH-modified samples and the effect of pH modifiers on trigeminal burn were examined employing a degree of difference test. The effect of the different pH modifiers on the levels of carbonyl species was also determined using the above-mentioned dynamic headspace GC/MS-SIM method.

Carbonyl Scavenger Treatments

Trehalose, a food grade naturally occurring disaccharide was employed based on its hypothesized reactivity towards carbonyls species at elevated pH values. Trehalose was incorporated in relatively low levels (0.2%) and sensory properties of the resulted samples were examined employing a degree-of-difference test. The effect of trehalose on the levels of carbonyl species was also determined using the above-mentioned dynamic headspace GC/MS-SIM method.

Results and Discussion

To investigate the sensorial effect of different pH modifiers, food grade sodium bicarbonate and sodium carbonate was compared to food grade sodium hydroxide. Panelists were asked to compare each pH-modified sample to a control (Karkov pH 3.0) and rate trigeminal burn and smoothness. The results revealed that all three pH modifiers had very similar effect on trigeminal burn reduction, but overall sodium carbonate generated a "cleaner" smoother product. Sensory results are shown in Table 23.

TABLE 23

Average (n = 6) degree of difference ratings for trigeminal burn of Karkov vodka samples treated with sodium dicarbonate (SB, pH 7.65), sodium carbonate (SC, pH 8.0) and sodium hydroxide (SH, pH 8.0) as compare to control (Karkov vodka pH 3.0).

| Sample | Rating[1] |
| --- | --- |
| Karkov (Blind control) | 0.30[a] |
| Karkov SB (pH 7.65) | −7.10[b] |
| Karkov SC (pH 8.0) | −8.40[c] |
| Karkov SH (pH 8.0) | −9.30[d] |

[1]Different letters indicate statistically significant difference determined by one-way ANOVA analysis and Dunnetts test ($\alpha = 0.05$);
[a]not significantly different than control.

Figure 20:
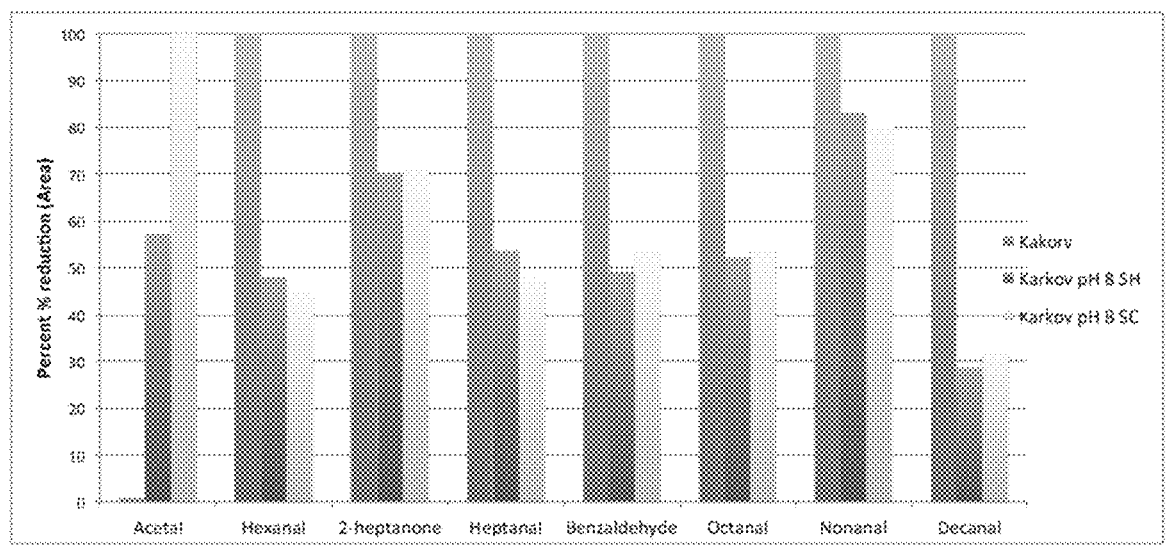
FIG. 20. Effect of sodium hydroxide and sodium bicarbonate on carbonyl species present in Karkov vodka. For each group, the following were tested and are shown from left to right: Karkov pH 3.0, Karkov pH 8.0 w/sodium hydroxide (SH), and Karkov pH 8.0 w/sodium carbonate (SC). Results are presented in area percent reduction and were obtained by DHS GC/MS-SIM. Highest peak area was adjusted to 100%.

The effect of sodium carbonate on the levels of carbonyl species as compared to sodium hydroxide and the original Karkov was also examined and the results are presented in FIG. 20. Both pH modifiers resulted in significantly lower levels of carbonyls when compared to the original Karkov vodka, a reduction between 30-70% for each compound was observed for the quantified aldehydes. Additionally the pH modifiers significantly increased the levels of acetal species further confirming the shift of the chemical balance towards the formation of acetal and hemi-acetal species.

Trehalose (Scheme 5) was also examined as a potential carbonyl scavenger when in combination with pH modifiers. Trehalose was expected to be more nucleophilic under alkaline conditions and thus more reactive towards electrophilic carbonyls such as aldehydes. Additionally trehalose is fairly cost effective and already has GRAS status thus making it a suitable choice for a potential ingredient technology. Trehalose was added (0.2% w/w) to Karkov vodka (pH 3.0) and pH modified Karkov vodka (pH 8.0). A degree-of-difference test was conducted in order to determine the trigeminal burn difference between trehalose and pH modified-trehalose treated samples as compared to original samples. Results (Table 24) demonstrate that the addition of trehalose significantly (p<0.05) reduced trigeminal burn perception in all tested samples. When trehalose addition was accompanied with pH modification the observed reduction of trigeminal burn was more pronounced suggesting higher trapping carbonyl reactivity under alkaline conditions.

Figure 21:
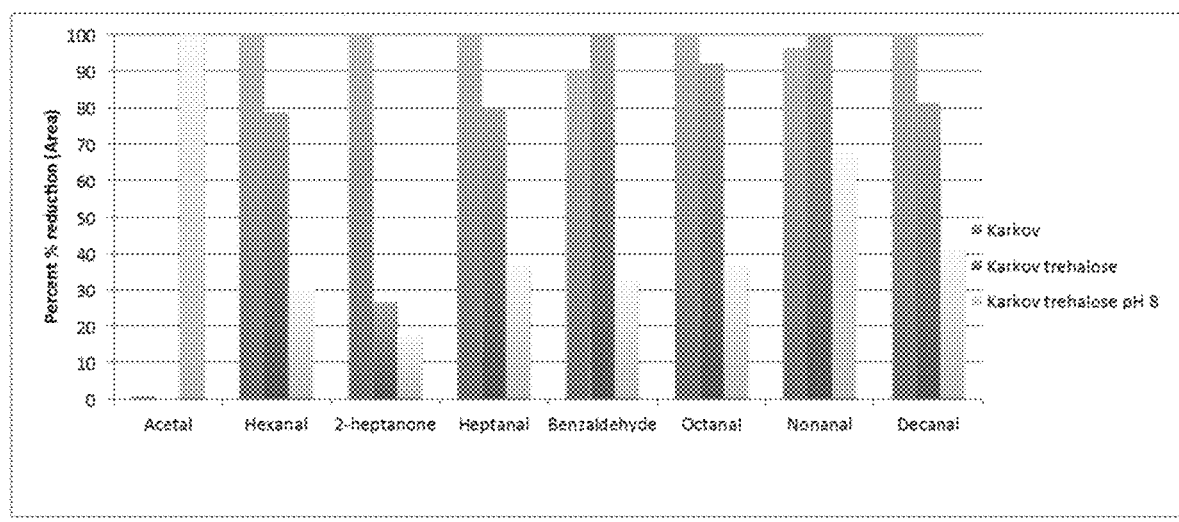
FIG. 21. Effect of trehalose on carbonyl species present in Karkov vodka. For each group, the following were tested and are shown from left to right: Karkov pH 3.0, Karkov pH 3.0 trehalose, Karkov pH 8.0 trehalose. Results are presented in area percent reduction and were obtained by DHS GC/MS-SIM. Highest peak area was adjusted to 100%.

Following the positive sensory results, the effect of trehalose on the concentration of carbonyl species was also examined and the results are presented in FIG. 21. Trehalose was found to reduce the concentration of carbonyl species when compared to original Karkov vodka. In addition, trehalose in combination with pH modification resulted in higher reduction of carbonyl species accompanied with a significant increase in acetal species (100-fold increase of acetaldehyde diethyl acetal). The analytical and sensorial data were in agreement supporting that the balance between carbonyl species and more specifically between carbonyls and their acetal/hemiacetal species affects the perceived trigeminal burn intensity and maturation with acetals having a positive impact.

TABLE 24

Average (n = 6) degree of difference ratings for trigeminal burn of Karkov vodka with and without pH modification or trehalose addition.

| Sample | Rating[1] |
| --- | --- |
| Karkov - Blind Control | 1.40[a]* |
| Karkov trehalose | −3.40[b] |
| Karkov pH 8.0 | −8.00[c] |
| Karkov pH 8.0 trehalose | −9.40[d] |

[1]Different letters indicate statistically significant difference determined by one-way ANOVA analysis and Dunnetts test (P < 0.05);
[a]not significantly different than control.

The results described herein support the importance of the balance between carbonyl and hemiacetal and acetal species in smoothness perception and the feasibility of pH adjustment and ingredient technologies as improvement strategies.

EXAMPLE 3

Sensory Recombination Study

A trained sensory panel consisting of 10 judges (ages 22 to 35) evaluated the trigeminal burn intensity of 60% water 40% ethanol solution, and a recombination model with added carbonyl species at levels quantified in 60% water 40% ethanol solutions when pH was adjusted at 3.0. Panelists were trained to recognize and focus on trigeminal burn and were asked to evaluate samples using a 10-point scale. Nanopure water and a Water/Ethanol (60/40) solution with high levels of added aldehydes (2 ppm) represented the edges of the reference scale namely, zero and ten, respectively. Samples were presented in a randomized order in three-digit coded cups and panelists were asked to rate each sample using the 10-point reference scale.

The trigeminal burn intensity of each individual carbonyl compound when added in a Water/Ethanol (60/40) solution was also evaluated at the corresponding concentration following the above mentioned sensory evaluation method. Added levels of each carbonyl compound are presented in Table 25.

TABLE 25

Concentration of carbonyls species added in Water/Ethanol (60/40) solution for the construction of recombination models. Concentration presented in parts per million (ppm) or mg/L.

| Compound | Concentration (ppm) |
| --- | --- |
| Hexanal | 0.48 |
| Heptanal | 0.50 |
| Octanal | 0.05 |
| Nonanal | 1.38 |
| Decanal | 2.11 |
| Benzaldehyde | 0.67 |
| 2-heptanone | 1.32 |

Result and Discussion

A more extensive recombination experiment was conducted to further confirm the sensory activity of carbonyl species and causality in trigeminal burn perception in alcohol containing products at their native levels. Both the contribution of individual carbonyl compounds as well as their combination on trigeminal burn was evaluated.

The contribution of the carbonyl mixture can further confirm causality regarding trigeminal burn perception and individual contribution can provide information on which components can exert the highest modulation on trigeminal burn both positive and negative. This approach can further lead to selection of control points for flavor improvement strategies as well as screening strategies for selection of raw materials (i.e. alcohol distillates) for production of alcohol containing products.

Sensory results (Table 26) revealed that the recombination model with water/ethanol and the added mixture of carbonyl compounds had a significantly higher trigeminal burn when compared to a water/ethanol solution with no carbonyls added. Thus, confirming causality of carbonyl species on trigeminal burn at their native levels and same pH systems.

TABLE 26

Average (n = 10) trigeminal burn rating of water/ethanol solution (60/40) with and without mixture of carbonyls compounds. Carbonyl compounds were added in levels quantified when pH of solution was adjusted to 3.0 (see Table 25).

| Sample | Rating |
| --- | --- |
| Water/ethanol | $6.00^a$ |
| Water/ethanol + carbonyls | $8.62^b$ |

[1]Different letters indicate statistically significant difference determined by one-way ANOVA analysis and Dunnetts test ($P < 0.05$)

When the contribution of individual carbonyl compounds on trigeminal burn at their native levels was evaluated results showed that all recombination models were rated higher than the Water/ethanol solution (6.0) (see Table 27). Though not all carbonyls were found to be significantly different than the control (i.e. hexanal, heptanal and decanal) an increasing trend was observed. The obtained information additionally facilitated the identification of the stronger causative agents regarding trigeminal burn intensity. Comparing added levels and intensity rating it becomes evident that octanal is a very potent trigeminal burn contributor as it elicited one of the highest ratings (7.13) at only 0.05 ppm (or 0.05 mg/L). Benzaldehyde also seemed to be a strong contributor followed by nonanal and 2-heptanone which had the highest intensity rating. Results further support the effect of carbonyl species on trigeminal burn perception and the selection of carbonyl species as chemical targets for the development of smoothness improvement strategies for alcohol containing products.

TABLE 27

Average (n = 10) trigeminal burn intensity rating of water/ethanol solution (60/40) with added carbonyl compounds. Individual carbonyl compounds were added in levels quantified when pH of solution was adjusted to 3.0 (see Table 25).

| Recombination sample | Rating |
| --- | --- |
| Water/ethanol | $6.00^a$ |
| Water/ethanol + hexanal | $6.75^a$ |
| Water/ethanol + heptanal | $6.25^a$ |
| Water/ethanol + octanal | $7.13^b$ |
| Water/ethanol + nonanal | $7.31^b$ |
| Water/ethanol + decanal | $6.56^a$ |
| Water/ethanol + bezaldehyde | $7.13^b$ |
| Water/ethanol + 2-heptanone | $7.56^b$ |

[1]Different letters indicate statistically significant difference determined by one-way ANOVA analysis and Dunnetts test ($P < 0.05$).

EXAMPLE 4

Using methods described herein (see, e.g., Examples 1-3), the pH-modified treatment (raised to 6, 7 and 8) was further demonstrated on select distilled spirits such as rum (Trader Vic's, US Distilled Products Co. Princeton, Minn.), tequila (Cabrito, US Distilled Products Co. Princeton, Minn.), and whiskey (Early Times, Brown-Forman Co., Louisville, Ky.). Sensory evaluation of these pH-modified samples confirmed there was a significant reduction of the perceived trigeminal burn intensity and a noted smoothness improvement in direct comparison to the unmodified samples.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of preparing a modified distilled alcoholic spirit that comprises an acetal or hemiacetal of cinnamic aldehyde and/or vanillin, comprising contacting a corresponding starting distilled alcoholic spirit comprising cinnamic aldehyde and/or vanillin with a base under conditions that cause the cinnamic aldehyde and/or vanillin to be converted to a corresponding acetal or hemiacetal, thereby providing the modified distilled alcoholic spirit, wherein the modified distilled alcoholic spirit is a whiskey, rum, brandy, tequila, soju, gin or baiju that has an alcohol by volume (ABV) of at least about 15%.

2. The method of claim 1, wherein the corresponding starting distilled alcoholic spirit comprises cinnamic aldehyde.

3. The method of claim 1, wherein the corresponding starting distilled alcoholic spirit comprises vanillin.

4. The method of claim 1, wherein the corresponding starting distilled alcoholic spirit comprises cinnamic aldehyde and vanillin.

5. The method of claim 1, wherein the modified distilled alcoholic spirit is whiskey, bourbon whiskey, rye whiskey, wheat whiskey, malt whiskey, rye malt whiskey, corn whiskey, straight bourbon whiskey, straight rye whiskey, straight wheat whiskey, straight malt whiskey, straight rye malt whiskey, straight corn whiskey, whiskey distilled from bourbon mash, light whiskey, blended whiskey, blend of straight whiskies, spirit whiskey, scotch whisky, Irish whiskey, Canadian whiskey, rum, fruit brandy, cognac, cognac brandy, dried fruit brandy, lees brandy, pomace brandy, mare brandy, residue brandy, neutral brandy, eau de vie, a substandard brandy, tequila, gin, dry gin, Geneva gin, or Old Tom Gin.

6. The method of claim 1, wherein the pH of the corresponding starting distilled alcoholic spirit is about 3.0 to about 5.5.

7. The method of claim 1, wherein the pH of the modified distilled alcoholic spirit is about 6.0 to about 8.5.

8. The method of claim 1, wherein the base is a food grade additive.

9. A method of preparing a modified distilled alcoholic spirit, comprising contacting a corresponding starting distilled alcoholic spirit comprising cinnamic aldehyde and/or vanillin with abase selected from the group consisting of sodium bicarbonate, sodium carbonate, sodium hydroxide, potassium hydroxide, potassium carbonate and potassium bicarbonate, under conditions that cause the cinnamic aldehyde and/or vanillin to be converted to a corresponding acetal or hemiacetal, thereby providing the modified distilled alcoholic spirit, wherein the modified distilled alcoholic spirit is a whiskey, rum, brandy, tequila, soju, gin or baiju that has an alcohol by volume (ABV) of at least about 15%.

10. The method of claim 1, wherein the amount of the cinnamic aldehyde and/or vanillin in the modified distilled alcoholic spirit is reduced by at least about 10% by weight, as compared to the corresponding starting distilled alcoholic spirit.

11. The method of claim 1, wherein a total amount of free carbonyls in the modified distilled alcoholic spirit is reduced by at least about 10% by weight, as compared to the corresponding starting distilled alcoholic spirit.

12. The method of claim 1, wherein the amount of at least one additional aldehyde or ketone in the modified distilled alcoholic spirit is reduced by at least about 10% by weight, as compared to the corresponding starting distilled alcoholic spirit.

13. The method of claim 12, wherein the amount of at least one additional aldehyde is reduced by at least about 10% by weight, wherein the aldehyde is selected from the group consisting of acetaldehyde, 2-methylbutanal, 3-methylbutanal, propanal, butanal, pentanal, hexanal, heptanal, octanal, nonanal, decanal, benzaldehyde, 2-propenal, 3-methyl-2-butenal, (E)-2-hexanal, (E)-2-octenal, (E)-2-nonenal and (E,E)-2,4-decadienal.

14. The method of claim 12, wherein the amount of at least one ketone is reduced by at least about 10% by weight, wherein the ketone is selected from the group consisting of 2-butanone, 2-pentanone, 2-heptanone, 2,3-butendione and 2,3-pentendione.

15. The method of claim 1, wherein the modified distilled alcoholic spirit has an alcohol by volume (ABV) of at least about 40%.

16. The method of claim 1, wherein the modified distilled alcoholic spirit has an alcohol by volume (ABV) of between about 40% to about 60%.

17. The method of claim 1, further comprising contacting the corresponding starting distilled alcoholic spirit and/or the modified distilled alcoholic spirit with a carbonyl scavenger agent.

18. The method of claim 1, wherein the trigeminal ethanol related burn, smoothness, taste, aroma and/or flavor profile of the modified distilled alcoholic spirit is improved over the corresponding starting distilled alcoholic spirit.

19. A method for preparing a modified whisky that comprises an acetal or hemiacetal of cinnamic aldehyde and/or vanillin and that has an alcohol by volume (ABV) of at least about 15% comprising, contacting a starting whisky that comprises cinnamic aldehyde and/or vanillin with a base under conditions that cause the cinnamic aldehyde and/or vanillin to be converted to a corresponding acetal or hemiacetal to provide the modified whisky that comprises an acetal or hemiacetal of cinnamic aldehyde and/or vanillin and that has an alcohol by volume (ABV) of at least about 15%.

20. The method of claim 19, wherein the modified whisky comprises cinnamaldehyde diethyl acetal or ethyl vanillin diethyl acetal.

21. The method of claim 1, wherein the modified distilled alcoholic spirit comprises cinnamaldehyde diethyl acetal or ethyl vanillin diethyl acetal.

22. A method of preparing a modified distilled alcoholic spirit that comprises an acetal or hemiacetal of cinnamic aldehyde and/or vanillin, comprising treating a starting distilled alcoholic spirit to increase the amount of cinnamic aldehyde and/or vanillin to provide a treated distilled alcoholic spirit having an increased amount of cinnamic aldehyde and/or vanillin; contacting the treated distilled alcoholic spirit with a base under conditions that increase the pH of the treated distilled alcoholic spirit from a range of about 3.0 to about 5.5 to a range of about 6.0 to about 8.5 to cause the cinnamic aldehyde and/or vanillin to be converted to a corresponding acetal or hemiacetal, thereby providing the modified distilled alcoholic spirit, wherein the modified distilled alcoholic spirit is a whiskey, rum, brandy, tequila, soju, gin or baiju that has an alcohol by volume (ABV) of at least about 15%.

23. The method of claim 22, wherein treating comprises aging.

24. The method of claim 19, wherein the method further comprises treating the starting whiskey to increase the amount of cinnamic aldehyde and/or vanillin to provide a treated distilled whiskey having an increased amount of cinnamic aldehyde and/or vanillin.

25. The method of claim 24, wherein contacting the starting whiskey further comprises contacting the treated distilled whiskey with the base under conditions that increase the pH of the treated distilled alcoholic spirit from a range of about 3.0 to about 5.5 to a range of about 6.0 to about 8.5.

26. A method of preparing a modified distilled alcoholic spirit that comprises an acetal or hemiacetal of cinnamic aldehyde and/or vanillin, comprising treating a starting distilled alcoholic spirit to increase the amount of cinnamic aldehyde and/or vanillin to provide a treated distilled alcoholic spirit having an increased amount of cinnamic aldehyde and/or vanillin; contacting the treated distilled alcoholic spirit with a base selected from the group consisting of sodium bicarbonate, sodium carbonate, sodium hydroxide, potassium hydroxide, potassium carbonate and potassium bicarbonate, under conditions that cause the cinnamic aldehyde and/or vanillin to be converted to a corresponding acetal or hemiacetal, thereby providing the modified distilled alcoholic spirit, wherein the modified distilled alcoholic spirit is a whiskey, rum, brandy, tequila, soju, gin or baiju that has an alcohol by volume (ABV) of at least about 15%.

* * * * *